US010647777B2

(12) United States Patent
Brower et al.

(10) Patent No.: US 10,647,777 B2
(45) Date of Patent: May 12, 2020

(54) METHODS OF CONTROLLING THE FORMATION OF DISULFIDE BONDS IN PROTEIN SOLUTIONS

(71) Applicant: Genzyme Corporation, Cambridge, MA (US)

(72) Inventors: Kevin P. Brower, Holliston, MA (US); Chris Hwang, Framingham, MA (US); Rao Koduri, Shrewsbury, MA (US); Konstantin B. Konstantinov, Waban, MA (US); Veena Warikoo, Westford, MA (US); Marcella Yu, Medford, MA (US); Jin Yin, Somerville, MA (US)

(73) Assignee: GENZYME CORPORATION, Cambridge, MA (US)

( * ) Notice: Subject to any disclaimer, the term of this patent is extended or adjusted under 35 U.S.C. 154(b) by 642 days.

(21) Appl. No.: 14/668,820

(22) Filed: Mar. 25, 2015

(65) Prior Publication Data
US 2016/0108127 A1 Apr. 21, 2016

Related U.S. Application Data

(60) Provisional application No. 62/004,175, filed on May 28, 2014.

(51) Int. Cl.
| | | |
|---|---|---|
| *C07K 1/113* | (2006.01) |
| *A61K 39/395* | (2006.01) |
| *C07K 16/28* | (2006.01) |
| *C07K 16/00* | (2006.01) |
| *C07K 16/22* | (2006.01) |

(52) U.S. Cl.
CPC .... *C07K 16/2896* (2013.01); *A61K 39/39591* (2013.01); *C07K 1/1133* (2013.01); *C07K 16/00* (2013.01); *C07K 16/22* (2013.01); *C07K 16/2839* (2013.01); *C07K 2317/30* (2013.01); *C07K 2317/52* (2013.01)

(58) Field of Classification Search
None
See application file for complete search history.

(56) References Cited

U.S. PATENT DOCUMENTS

| | | | |
|---|---|---|---|
| 4,470,925 A | 9/1984 | Auditore-Hargreaves | |
| 2002/0115834 A1* | 8/2002 | Cerletti | C07K 14/495 530/399 |
| 2011/0086366 A1 | 4/2011 | Labrijn et al. | |
| 2012/0251541 A1 | 10/2012 | Baurin et al. | |
| 2013/0259882 A1 | 10/2013 | Liu | |
| 2014/0336361 A1* | 11/2014 | Giese | C07K 16/468 530/387.3 |
| 2016/0060291 A1* | 3/2016 | Krishnan | C07K 14/535 530/303 |

FOREIGN PATENT DOCUMENTS

| | | | | |
|---|---|---|---|---|
| WO | WO 2006/047340 A2 | 5/2006 | | |
| WO | WO 2008119353 A1 * | 10/2008 | ............. | C07K 16/00 |
| WO | WO 2009/103791 A1 | 8/2009 | | |
| WO | WO 2011131746 A2 * | 10/2011 | ......... | C07K 16/1063 |
| WO | WO 2013060867 A2 * | 5/2013 | ......... | C07K 16/2863 |

OTHER PUBLICATIONS

The International Search Report and Written Opinion of the International Searching Authority for International Application No. PCT/US2015033048; dated Aug. 5, 2015, pp. 1-13.
Deng et al., "Detection and Quantification of the Human IGG4 Half-Molecule, HL, From Unpurified Cell-Culture Supernatants", Biotechnology and Applied Biochemistry, 40 (Pt.3):261-69 (Dec. 2004).
Gramer et al., "Production of 1-38 stable bispecific IgG1 by controlled Fab-arm exchange" MABS, 5(6):962-73 (Nov. 2013).
Labrijn et al., "Efficient generation of stable bispecific IgGl by controlled Fab-arm exchange" Proceedings of the National Academy of Sciences, 118(13):5145-58 (Mar. 2013).
Rispens et al., "Mechanism of Immunoglobulin G4 Fab-arm Exchange" Journal of the American Chemical Society, 133(26):10302-311 (Jul. 2011).
Schuurman et al., "Opening the door to innovation" MABS, 6(4):812-19 (Apr. 2014).
Angal et al., "A single amino acid substitution abolishes the heterogeneity of chimeric mouse/human (IgG4) antibody." Mol. Immunol. 30(1):105-8 (Jan. 1993).
Bloom et al., "Intrachain disulfide bond in the core hinge region of human IgG4." Protein Sci. 6(2):407-15 (Feb. 1997).
Bruggemann et al., "Comparison of the effector functions of human immunoglobulins using a matched set of chimeric antibodies." J Exp. Med. 166(5):1351-61 (Nov. 1987).
Jones et al., "Replacing the complementarity-determining regions in a human antibody with those from a mouse." Nature 321:522-525 (May-Jun. 1986).
King et al., "Expression, purification and characterization of a mouse-human chimeric antibody and chimeric Fab' fragment." Biochem J. 281(2):317-23 (Jan. 1992).
Labrijn et al., "Efficient generation of stable bispecific IgG1 by controlled Fab-arm exchange." Proc Nat'l Acad Sci USA. 110(13):5145-50 (Epub Mar. 11, 2013).
Labrijn et al., "Therapeutic IgG4 antibodies engage in Fab-arm exchange with endogenous human IgG4 in vivo." Nature Biotechnol. 27(8):767-771 (Aug. 2009).
Miesegaes et al., "Monoclonal antibody capture and viral clearance by cation exchange chromatography" Biotechnol Bioeng. 109(8):2048-58 (Epub Apr. 8, 2012).
Palmer et al., "Reduction and Reoxidation of a Critical Disulfide Bond in the Rabbit Antibody Molecule," J Biol. Chem., 238(7):2393-2398 (Jul. 1963).

(Continued)

Primary Examiner — Daniel E Kolker
Assistant Examiner — James L Rogers
(74) Attorney, Agent, or Firm — McDonnell Boehnen Hulbert & Berghoff LLP

(57) ABSTRACT

Disclosed herein are methods that have been developed to control the formation of disulfide bonds between polypeptides of a multimeric protein produced by a bioprocess. Also disclosed are protein solution parameters that allow for controlling the formation of disulfide bonds. In one example, the methods disclosed herein can be used to control the proportion of half antibody molecules in an antibody solution.

31 Claims, 12 Drawing Sheets

(56) References Cited

OTHER PUBLICATIONS

Presta, "Antibody Engineering" Curr. Op. Struct. Biol. 2:593-596 (Aug. 1992).
Riechmann et al., "Reshaping human antibodies for therapy" Nature 332:323-329 (Mar. 1988).
Rispens et al., "Mechanism of immunoglobulin G4 Fab-arm exchange." J Am Chem Soc. 133(26):10302-10311 (Epub Jun. 15, 2011).
Rose et al., "Quantitative analysis of the interaction strength and dynamics of human IgG4 half molecules by native mass spectrometry." Structure, 19(9):1274-82 (Sep. 2011).
Schuurman et al., "The inter-heavy chain disulfide bonds of IgG4 are in equilibrium with intra-chain disulfide bonds" Mol Immunol. 38(1):1-8 (Jan. 2001).
Spiegelberg et al., "Human myeloma IgG half-molecules. Structural and antigenic analyses" Biochemistry 14 (10):2157-63 (May 1975).
Taylor et al., "Suppression of sodium dodecyl sulfate-polyacrylamide gel electrophoresis sample preparation artifacts for analysis of IgG4 half-antibody." Anal Biochem. 353(2):204-208 (Epub Mar. 9, 2006).
Zohren et al., "The monoclonal anti-VLA-4 antibody natalizumab mobilizes CD34+ hematopoietic progenitor cells in humans." Blood 111:3893-3895 (Epub Jan. 30, 2008).

\* cited by examiner

METHODS OF CONTROLLING THE FORMATION OF DISULFIDE BONDS IN PROTEIN SOLUTIONS

RELATED APPLICATION

This application claims the benefit of U.S. Provisional Application No. 62/004,175, filed May 28, 2014, the disclosure of which is explicitly incorporated by reference herein.

TECHNICAL FIELD

The invention relates to methods of biotechnology and the biomanufacturing of recombinant proteins and antibodies.

BACKGROUND OF THE INVENTION

Disulfide bond formation between polypeptides of a protein is a critical aspect of proper protein assembly and structure. Protein multimerization may be dependent on sufficient levels of disulfide bond formation between polypeptides (e.g. polypeptide monomers/multimers). Antibodies represent one class of proteins that is particularly dependent on disulfide bond formation.

Antibodies are generally composed of four polypeptides, two light chains and two heavy chains (L:H:H:L). Most antibodies contain disulfide bonds between the four polypeptide chains. Occasionally, the disulfide bonds between the heavy chain polypeptides are not formed, resulting in the formation of an antibody comprising no interchain disulfide bonds between the two pairs of heavy and light chains. See, generally, FIG. 1. These antibodies have been termed half antibodies (abbreviated herein as "Hab").

Certain antibody classes and types are more susceptible to half antibody formation, such as the immunoglobulin G, subclass 4 (abbreviated herein as "IgG4") antibodies. In both natural and recombinant antibody production, a significant proportion of IgG4 antibodies, at least as high as 35%, are produced as half antibodies. (Miesages et al., 2012, *Biotechnol Bioeng.* 109(8): 2048-58).

Under physiological conditions, half antibodies typically exist as complete, functional antibodies due to strong non-covalent interactions between the two heavy chain-light chain antibody halves, despite the absence of interchain disulfide bonds. (Rose et al., 2011, *Structure*, 19(9):1274-82). Half antibody formation has been associated with formation of aberrant proteins (See FIG. 1). For example, half-antibody formation in IgG4 antibodies may be due to the primary amino acid sequence and structure of the hinge region, which results in the ability of IgG4 antibodies to perform dynamic Fab arm exchange in which two antibodies can recombine with one another to form bispecific antibodies. (See, e.g., U.S. Pat. No. 4,470,925; U.S. Patent Application Publication No. US 2011/0086366 A1). This feature of the IgG4 subtype may be accounted for by the increased flexibility of the hinge sequence that makes it easier to form the cyclic intra-chain disulfide bond. (Bloom et al., 1997, *Protein Sci.* 6(2):407-15; Schuurman et al., 2001, *Mol Immunol.* 38(1):1-8). Half antibody formation may also be traced to deletions in the heavy chain constant domains, such as with antibodies produced by certain myelomas (Spiegelberg et al., 1975, *Biochemistry* 14(10):2157-63).

Half antibodies are not currently known to be associated with any distinct clinical syndrome or toxicology. However, the level of half antibody is a critical quality attribute for the production and/or manufacturing of therapeutic IgG4 antibodies. The extent to which upstream or downstream antibody processing conditions can be used to control the formation of disulfide bonds between polypeptides of multimeric proteins in final drug substances is poorly understood.

SUMMARY OF THE INVENTION

The invention as disclosed herein encompasses a methodology that has been developed to control the formation of disulfide bonds between polypeptides of a protein produced by a bioprocess. In one aspect, the invention comprises methods for controlling the number of disulfide bonds between polypeptides of a multimeric protein produced by a bioprocess. Certain embodiments of this aspect comprise the following steps: (a) contacting the polypeptides with a conditioned solution at a specific time point during the bioprocess, wherein the conditioned solution comprises one or more predetermined solution parameters, and (b) incubating the conditioned solution comprising the polypeptides for a predetermined time at a predetermined temperature, wherein the incubation of the polypeptides with the conditioned solution controls the formation of disulfide bonds between the polypeptides of the protein. In certain embodiments, when the disclosed methods are applied, the number of disulfide bonds between the polypeptides of the protein is increased. In other embodiments, the number of disulfide bonds between the polypeptides of the protein is decreased. In yet other embodiments, the number of disulfide bonds between the polypeptides of the protein is maintained.

In certain embodiments of the disclosed methods the predetermined solution parameters comprise one or more of the following: redox reagent identity, redox reagent concentration, pH, gas identity, dissolved gas levels, conductivity, and viable cell density.

In certain embodiments of the disclosed methods the redox reagent identity is 2-mercaptoethylamine (2-MEA), reduced glutathione, oxidized glutathione, 2-mercaptoethanol, dithiothreitol (DTT), cysteine, cystine, dithiobutylamine, or sodium sulfite. In some of these embodiments the redox reagent identity is 2-MEA. In some of these embodiments the ratio of redox reagent molarity to protein molarity is at least 4:1, 8:1, 16:1, or 32:1.

In certain embodiments of the disclosed methods the predetermined temperature of the incubation is between about 2° C. and about 23° C. In other embodiments, the predetermined temperature of the incubation is between about 23° C. and about 37° C. or higher. In some embodiments of the disclosed methods the conditioned solution comprising the polypeptides of the multimeric protein is mixed during incubation.

In some embodiments, the bioprocess of the disclosed methods comprises a batch, semi-continuous, or continuous bioprocess. In some embodiments, the polypeptides of the multimeric protein are contacted with a conditioned solution at a specific time point during the bioprocess that occurs after a bioreactor operation and/or fed batch cell culture operation in the bioprocess.

In certain embodiments, the disclosed methods further comprise the step of removing the polypeptides from the bioprocess at the specific time point during the bioprocess. In some of these embodiments, the disclosed methods further comprise the step of returning the polypeptides to the bioprocess after incubation.

In another aspect of the disclosed methods, the polypeptides of the multimeric protein are contacted with a conditioned solution at a specific time point during the bioprocess when the polypeptides are in a solution comprising a plurality of cells. In some of these embodiments, the specific time point is a time point when the polypeptides are located in a bioreactor, holding tank, or a non-bioreactor unit operation vessel comprising a plurality of cells.

In another aspect of the disclosed methods, the polypeptides of the multimeric protein are contacted with a conditioned solution at a specific time point when the polypeptides of the multimeric protein are in a cell-free solution. In some of these embodiments, the specific time point occurs during the step of viral inactivation, adjustment, chromatography, filtration, dilution, concentration, or any bioprocess step that is cell-free. In other embodiments, the specific time point occurs during the clarification stage, clarified harvest stage, capture stage, intermediate chromatography stage, or polishing chromatography stage of the bioprocess. In some of these embodiments, the specific time point during the bioprocess comprises a time point wherein the polypeptides are located in a holding tank. In certain other embodiments, the pH of the conditioned solution comprising the polypeptides after the incubation step is between about 3.0 and about 5.0.

In one embodiment, the cell-free solution containing the polypeptides of the multimeric protein comprises Protein A eluate. In another embodiment, the cell-free solution containing the polypeptides of the multimeric protein comprises clarified harvest.

In some embodiments of the disclosed methods, the polypeptides of the multimeric protein are monomers of the protein. In other embodiments, the polypeptides of the multimeric protein are multimers of the protein.

In another aspect, the multimeric protein that is controlled according to the disclosed methods is an antibody. In some of these embodiments, the polypeptides of the multimeric protein comprise heavy chain polypeptides. In other embodiments, the polypeptides of the multimeric protein comprise light chain polypeptides. In yet other embodiments, the polypeptides of the multimeric protein comprise heavy chain polypeptides and light chain polypeptides. In one embodiment, the antibody of the disclosed methods is an IgG4 antibody.

In another embodiment, the antibody of the disclosed methods comprises natalizumab, gemtuzumab, or fresolimumab.

In another aspect, the multimeric protein that is controlled according to the disclosed methods is an antibody fragment. In some of these embodiments, the polypeptides of the multimeric protein comprise heavy chain polypeptides. In other embodiments, the polypeptides of the multimeric protein comprise light chain polypeptides. In yet other embodiments, the polypeptides of the multimeric protein comprise heavy chain polypeptides and light chain polypeptides. In one embodiment, the antibody fragment of the disclosed methods is an IgG4 antibody fragment.

In yet another aspect, the multimeric protein that is controlled according to the disclosed methods is a non-antibody protein. In certain embodiments, the non-antibody protein is an enzyme.

In another aspect, disclosed herein is a method of controlling the proportion of half antibody molecules in a solution comprising a population of antibody molecules. Certain embodiments of this aspect comprise the following steps: (a) contacting the solution comprising the population of antibody molecules with a conditioned solution, wherein the conditioned solution comprises predetermined solution parameters, and (b) incubating the conditioned solution comprising the antibody molecules for a predetermined time at a predetermined temperature, wherein the incubation of the antibody molecules with the conditioned solution controls the proportion of half antibody molecules in the conditioned antibody solution. In certain embodiments of this aspect the predetermined solution parameters comprise redox reagent selection, redox reagent concentration, pH, gas selection, dissolved gas levels, conductivity, viable cell density, and/or protein concentration.

In some embodiments, the proportion of half antibody molecules in the conditioned antibody solution is less than 30 percent (%). In other embodiments, the proportion of half antibody molecules in the conditioned antibody solution is less than 20 percent (%). In still other embodiments, the proportion of half antibody molecules in the conditioned antibody solution is less than 15 percent (%).

DESCRIPTION OF DRAWINGS

FIG. 1, row A depicts a full antibody (left) and a half antibody (right) in which the protein monomer sub-units (thick lines) are associated with one another by disulfide bonds (thin lines) and strong non-covalent interactions (asterisks). In this example, full antibodies contain disulfide bonds between all multimeric sub-units, including interchain disulfides between the two larger heavy chain sub-units. In a half antibody, the interchain disulfide bonds exist, instead, as intrachain disulfide bonds such that no covalent bond exists between the heavy chain sub-units. However, strong non-covalent interactions maintain a strong association between the two heavy chain sub-units. The full or half antibodies may have specificity for a single target or for two different targets (bispecificity). FIG. 1, row B depicts antibody fragments connected to one another via interchain disulfide bonds (left) or completely separate from one another (right) in the case of intrachain disulfide bonds within the fragment. In this case, due to the absence of certain segments of the protein, strong non-covalent interactions do not exist between the fragments and, consequently, the antibody fragments are not associated with one another when intrachain disulfide bonds are present. These fragments may have specificity for the same target or for two different targets (bispecificity).

In FIG. 3, graph A, the half antibody content was measured as a function of hold time at three different temperatures: 8° C./Cold (circles), 21° C./Ambient (squares), or 37° C./Warm (triangles). In FIG. 3, graph C, the half antibody content was measured as a function of hold time for either mixed samples (circles) or unmixed low VCD samples (diamonds). Viable cell density in millions of cells per mL ($\times 10^6$ cells per mL) is shown as a function of hold time (in days) is depicted in FIG. 3, graphs B and D. In FIG. 3, graph B, the half antibody content was measured as a function of hold time at three different temperatures: 8° C./Cold (circles), 21° C./Ambient (squares), or 37° C./Warm (triangles). In FIG. 3, graph D, the half antibody content was measured as a function of hold time as either mixed samples (circles) or unmixed low VCD samples (diamonds).

FIG. 9 depicts the half antibody proportions of each sample over the first two hours with or without treatment with 2-MEA. Test conditions included room temperature (21° C.) without 2-MEA added (circles), room temperature (21° C.) with 2-MEA added (diamonds), 8° C. without 2-MEA added (squares), and 8° C. without 2-MEA added (triangles).

FIG. 10 depicts the half antibody proportions each sample over 7 days (168 hours) with or without treatment with 2-MEA. Test conditions included room temperature (21° C.) without 2-MEA added (circles), room temperature (21° C.) with 2-MEA added (diamonds), 8° C. without 2-MEA added (squares), and 8° C. without 2-MEA added (triangles).

DETAILED DESCRIPTION OF THE INVENTION

Figure 2:
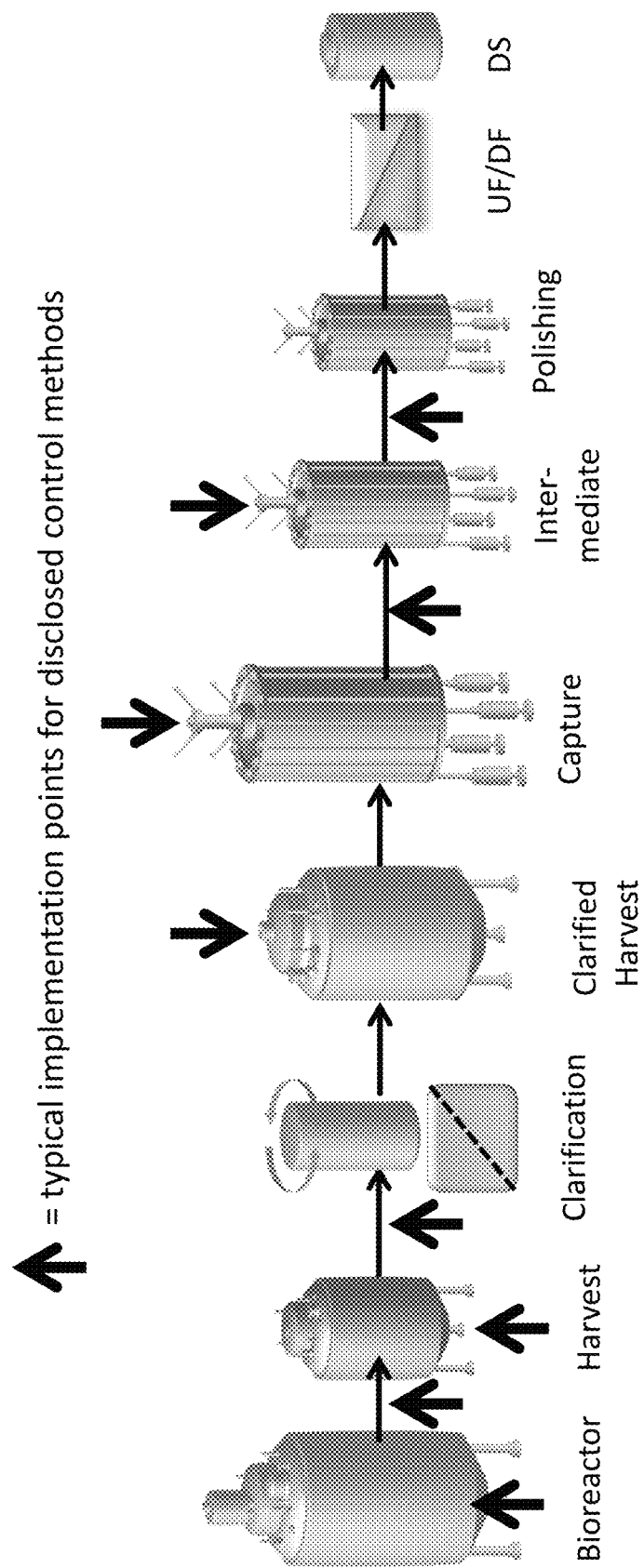
FIG. 2: Schematic representation of unit operations of a bioprocess comprising various time points for implementation of the disclosed methods. Methods can be implemented (1) within unit operations, such as by addition to a bioreactor or inclusion in a wash step on a chromatography column, (2) between unit operations, such as during transfer between a bioreactor and harvest hold tank, or (3) during a hold step for a process intermediate, such as a chromatography eluate or bioreactor harvest. Alternative bioprocess schemes are possible, including inclusion of different or additional unit operations within the bioprocess. Examples of alterations include alternative clarification operations (other than centrifugation and depth filtration) or inclusion of an additional chromatography step.

This disclosure comprises methods of controlling the formation of disulfide bonds between polypeptides of a protein produced by a bioprocess. One way to measure the formation (e.g. number) of disulfide bonds between polypeptides is to measure the proportion of half antibody (Hab) molecules present in a solution comprising a population of antibody molecules. By measuring the effect of a conditioned solution on the level of half antibody present in an immunoglobulin G, subclass 4 (IgG4) antibody solution, the effect of the conditioned solution on disulfide bond formation between polypeptides is measured. As disclosed herein, certain parameters of a polypeptide-containing solution have an unexpected and potent effect on the formation of disulfide bonds between polypeptides. A number of methods are disclosed to control disulfide bond formation, including strategies to decrease, increase, or maintain the levels of disulfide bond formation between polypeptides. As disclosed in detail herein, these methods can be applied at multiple points within a typical bioprocess used for protein production, including for example the production of antibody proteins or antibody fragments. (FIG. 2).

IgG4s possess several properties that make them attractive therapeutic candidates as well as an excellent model for measuring disulfide bond formation between polypeptides. For example, IgG4s have long serum half-lives and low Fc function and/or effector function. (Bruggemann et al., 1987, *J Exp. Med.* 166(5):1351-61). However, IgG4 antibodies also have unusual properties which are undesirable in vivo: IgG4 antibodies are unstable, dynamic molecules which engage in Fab arm exchange. An administered therapeutic IgG4 antibody may exchange with endogenous IgG4 antibodies with undesired specificities. The random nature of this process introduces unpredictability, which is highly undesirable for human immunotherapy.

These uncertainties surrounding the role of IgG4 Fab arm exchange and the in vivo impact of half antibodies make it desirable to minimize the level of half antibodies present in a final therapeutic antibody composition. Previously, Hab proportions were decreased by mutation of the amino acid sequence of the IgG4 antibody hinge region to that of an IgG1 hinge region, which has been shown to markedly stabilize the covalent disulfide interaction between the IgG4 heavy-chains (Angal et al., 1993, *Mol. Immunol.* 30(1):105-8; Schuurman et al., 2001; U.S. Patent Application Publication No. US 2011/0086366 A1). Altering the amino acid sequence and the resulting protein structure of an antibody, especially for a therapeutic antibody already under active clinical study, presents both scientific and regulatory challenges. As a result, this mutagenesis strategy cannot be applied in many situations where clinical and even preclinical experience with a therapeutic IgG4 having certain levels of half antibody has been significant. Therefore, strategies to control levels of half antibody levels must be established to ensure molecular consistency throughout subsequent clinical study and commercialization of the therapeutic IgG4 molecule.

The methods disclosed herein comprise multiple processes for controlling the formation of disulfide bonds between polypeptides of a multimeric protein produced by a bioprocess. The methods disclosed herein include cell-containing and cell-free methods which apply conditioned solutions comprising predetermined solution parameters, including redox reagent identity, redox reagent concentration, pH, gas identity, dissolved gas levels, conductivity, and/or viable cell density. These methods can be implemented at one or more points within a bioprocess to control, decrease, increase, or maintain the formation of disulfide bonds between polypeptides of a multimeric protein, such as for example those between the heavy chains of an IgG4 antibody. Control of the formation of disulfide bonds between polypeptide monomers and/or multimers is required to achieve product quality consistency within the life cycle of a multimeric protein product or when producing bioequivalent or biosimilar versions of a multimeric protein.

Conditioned Solutions

In one aspect, the methods presented herein disclose contacting the polypeptides of the protein with a "conditioned solution" which has been optimized to produce the desired formation or number of disulfide bonds between polypeptides. This conditioned solution has been predetermined to control the formation of disulfide bonds as desired. In certain embodiments, the conditioned solution has been predetermined to decrease the number of disulfide bonds between the polypeptides of the protein. In other embodiments, the conditioned solution has been predetermined to increase the number of disulfide bonds between the polypeptides of the protein. In yet other embodiments, the conditioned solution has been predetermined to maintain the number of disulfide bonds between the polypeptides of the protein. The effect of incubation conditions and predetermined condition parameters on disulfide bond formation can be demonstrated by measuring the proportion of IgG4 half antibody present in the protein solution. In some embodiments of the disclosed methods, the proportion of half antibody molecules (Hab) in a solution comprising a multimeric protein is determined. The determination of the proportion of half antibody molecules can be used as a method of measuring the disulfide bond formation between polypeptides of the multimeric protein.

A "conditioned solution" as used according to the disclosed methods comprises one or more predetermined solution parameters. Before applying the disclosed methods to a bioprocess that produces a protein, in certain embodiments, the parameters of the conditioned solution are determined before the methods are applied to the bioprocess being used to produce the protein of interest. In one aspect of the methods, the conditioned solution is cell-containing. In another aspect, the conditioned solution is cell-free. Additional details regarding each of these aspects are disclosed elsewhere in the specification (see below).

The control of the formation or number of disulfide bonds may be influenced by the properties of the specific polypeptide, protein, and/or protein class selected for application of the methods. The control of the formation of disulfide bonds may also be influenced by the properties of bioprocess used to produce the protein of interest, including for example the design of the bioprocess and the properties of the unit operations comprising the bioprocess. Therefore, it may be necessary to perform preliminary test studies to optimize one or more conditioned solution parameters to achieve the desired result with the selected protein and bioprocess. Non-limiting examples of such test studies and experiments are disclosed herein (see "Examples" section, below)

The different predetermined solution conditions disclosed herein can be applied either independently or in combination with the other predetermined solution conditions. For an exemplary study, see Table 2 (below). Each of the conditions disclosed herein provides some level of control over disulfide bond formation between protein polypeptides according to the methods disclosed. One predetermined solution condition may influence one or more of the other predetermined solution conditions in any given solution. In some scenarios, some predetermined solution conditions will be "complementary" to one or more of the other predetermined solution conditions, which will allow for the use of less extreme conditions to produce the desired disulfide bond formation result. For example, the use of a particular gas and gas pressure (e.g. oxygen) in the solution may require a reduced concentration of redox reagent to achieve the same result as a solution where the particular gas is not used. In certain embodiments, the application of a combination of predetermined solution conditions produces an additive effect on the formation of disulfide bonds. In other embodiments, the application of a combination of predetermined solution conditions produces a synergistic effect on the formation of disulfide bonds.

As used herein, the term "predetermined solution parameters" refers to one or more parameters, properties, qualities, composition, content, and/or other attributes of a solution.

In some applications of the disclosed methods the proportion of Hab molecules in solution is the desired disulfide bond formation result. In one aspect, the disclosed methods are used to control the proportion of half antibody molecules in a solution comprising a population of antibody molecules. In these applications the disclosed methods are used to control the disulfide bonds involved in the formation of Hab. The methods are capable of producing a conditioned antibody solution with a desired proportion of Hab molecules.

In some embodiments, the desired proportion of Hab molecules in a solution is selected as an absolute amount or a range of absolute amounts. By using the disclosed methods, the proportion of Hab molecules in the solution can be controlled to target a desired absolute amount or proportion of Hab. It is possible to use the disclosed methods to either increase or decrease the proportion of Hab. In certain embodiments, the desired proportion of Hab molecules in the solution is less than 5%, about 5-10%, 10-15%, 15-20%, 20-25%, 25-30%, 30-50%, or greater than 50%.

In other embodiments, the desired proportion of Hab molecules in a solution is selected as a percent change or a range of percent changes (such as percent increase or decrease), as compared to the solution before application of the disclosed methods. By using the disclosed methods, the proportion of Hab molecules in the solution can be controlled to target a desired percent change in proportion of Hab.

In some embodiments, the desired change in the proportion of Hab molecules in the solution is a decrease of about 1%, 2%, 5%, 10%, 15%, 20%, 25%, 50%, or more. In certain other embodiments, the desired change in the proportion of Hab molecules in the solution is a decrease of about 1-5%, 5-10%, 10-15%, 15-20%, 20-25%, 25-30%, 30-50%, or greater than 50%. In yet other embodiments, the desired change in the proportion of Hab molecules in the solution is a decrease of about 1-50%.

In other embodiments, the desired change in the proportion of Hab molecules in the solution is an increase of about 1%, 2%, 5%, 10%, 15%, 20%, 25%, 50%, or more. In certain other embodiments, the desired change in the proportion of Hab molecules in the solution is an increase of about 1-5%, 5-10%, 10-15%, 15-20%, 20-25%, 25-30%, 30-50%, or greater than 50%. In yet other embodiments, the desired change in the proportion of Hab molecules in the solution is an increase of about 1-50%.

Redox Reagents

In one aspect of the disclosed methods, a predetermined solution parameter is the identity of redox reagent used in the conditioned solution. As used herein, the term "redox reagent" refers to an agent containing in a mixture its reduced form, its oxidized form, or a combination of its reduced form and its oxidized form. According to the disclosed methods, a redox reagent may be present or absent in the conditioned solution depending on the desired disulfide bond formation result for the specific protein and/or bioprocess. In the embodiments where a redox reagent is present in the conditioned solution, a specific redox reagent is identified for inclusion in the conditioned solution.

Non-limiting examples of redox reagents that are suitable for the disclosed methods include 2-mercaptoethylamine (2-MEA), reduced glutathione, oxidized glutathione, 2-mercaptoethanol, dithiothreitol (DTT), cysteine, cystine, dithiobutylamine, and sodium sulfite. Certain redox reagents may produce superior results depending on the particular protein and/or solution. One of ordinary skill is capable of identifying, selecting, and testing different redox reagents on a particular protein solution to determine which redox reagent to use according to the disclosed methods. (See, e.g., U.S. Patent Application Publication No. US 20130259882 A1). In certain embodiments, the redox reagent used in the methods disclosed herein is mercaptoethylamine (2-MEA). 2-MEA has been shown to specifically reduce the hinge-region disulfide bonds of IgG4s. (Palmer et al., 1963, *J Biol. Chem.*, 238(7):2393-2398).

The use of redox reagents has been studied in the antibody field for different purposes. For example, redox reagents like 2-mercaptoethylamine (2-MEA) have been used to specifically reduce the interchain disulfide bond between the two Fab arms in order to promote Fab arm exchange. (King et al., 1992, *Biochem J.* 281(2):317-23).

In certain embodiments of the disclosed methods, one predetermined solution parameter is the redox reagent concentration in the conditioned solution. A range of concentrations of the selected redox reagent(s) can be used according to the methods disclosed. Once a redox reagent is selected, the redox reagent concentration must be optimized according to the selected redox reagent, protein, and/or bioprocess. In some embodiments of the methods where redox reagent is present in the conditioned solution, lower concentrations of redox reagent in the conditioned solution will result in the increased formation of disulfide bonds between protein polypeptides. For example, in one experiment, the use of lower concentrations of redox reagent in the conditioned solution results in a decrease in the proportion of half antibody molecules in a population of antibody molecules in solution (Table 2).

In other embodiments of the methods where redox reagent is present in the conditioned solution, higher concentrations of redox reagent in the conditioned solution will result in the decreased formation or number of disulfide bonds between protein polypeptides. For example, in one experiment, the use of higher concentrations of redox reagent in the conditioned solution results in an increase in the proportion of half antibody molecules in a population of antibody molecules in solution. (Table 2).

In certain embodiments, the optimal concentration of redox reagent comprises 0.01, 0.1, 0.5, 1, 2, 5, 25, 50 mM, or higher.

The optimal concentration of redox reagent may also be influenced by the concentration of protein or polypeptides in the solution. Therefore, in certain embodiments, the ratio of redox reagent concentration to protein concentration may be evaluated when determining the optimal redox reagent parameters in the conditioned solution. The ratio of redox reagent concentration to protein concentration may be determined in addition to, or alternatively to, the redox reagent concentration determination for the conditioned solution.

In certain embodiments, the optimal ratio of redox reagent molarity to protein molarity comprises at least 2:1, 4:1, 8:1, 16:1, 32:1, 64:1, 72:1, 88:1, 100:1, or higher. In certain embodiments of the methods, such as certain cell-free protein solutions, the ratio of redox reagent molarity to protein molarity comprises about 4:1 to about 40:1.

Incubation Time

In another aspect of the disclosed methods, the conditioned solution is incubated with the polypeptides of the multimeric protein for a predetermined time. As seen with other aspects of the disclosed methods, the predetermined incubation time may be influenced by the properties of the protein, bioprocess, and/or other solution conditions selected for application of the methods. Depending on the predetermined solution parameters of the conditioned solution, the incubation time could be as short as 1 minute or less or longer than a week or more. For example, if the concentration of redox reagent in the conditioned solution is high, the incubation time may have to be short to avoid damaging the protein. Conversely, if the concentration of redox reagent is low, the incubation time may have to be longer to achieve the desired control of disulfide bonds. As another illustrative example, if incubating a protein for an extended time period at a specific pH may result in protein instability, the same protein may remain stable at the same specific pH if incubated for only a short duration. Thus, more extreme pH values may be applied to some proteins if incubation times are adjusted accordingly to minimize protein instability.

Figure 3:
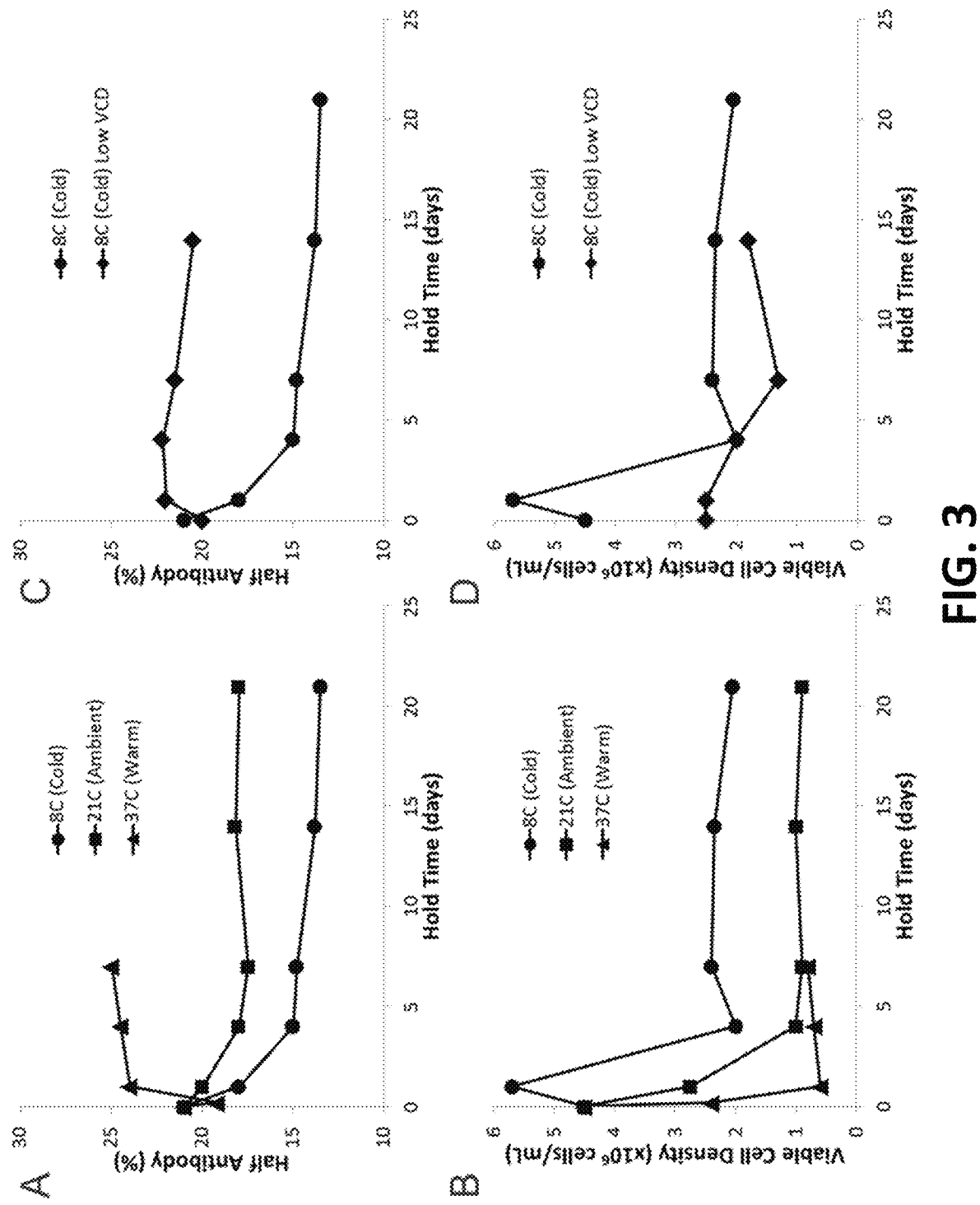
FIG. 3 depicts the cell-containing (unclarified harvest) hold study in which hold time, temperature, and initial viable cell density (VCD) were varied. Half antibody content in percentage of total antibody molecules is shown as a function of hold time (in days) in FIG. 3, graphs A and C.

Additional non-limiting examples of such test studies and experiments are disclosed in Example 2 and FIG. 3.

Incubation Temperature

In another aspect of the disclosed methods, the conditioned solution is incubated with the polypeptides at a predetermined temperature. As seen with other aspects of the disclosed methods, the predetermined incubation temperature may be influenced by the properties of the protein, bioprocess, and/or other solution conditions selected for application of the methods. Furthermore, different proteins comprise different stabilities at certain temperatures. For example, the desired result may occur faster or slower depending on the temperature of the incubation. In certain embodiments, the temperature can be decreased to order to promote disulfide bond formation and conversion of half antibody to full antibodies. In other embodiments, the temperature can be increased to promote conversion of full antibodies to half antibody. Additional non-limiting examples of such test studies and experiments are disclosed in Example 4 and FIG. 3.

In certain embodiments of the disclosed methods, the conditioned solution is incubated with the polypeptides at a predetermined temperature of about 2° C. to about 40° C.

pH

In another aspect of the disclosed methods, one predetermined solution parameter of the conditioned solution is the pH of the conditioned solution. As seen with other aspects of the disclosed methods, the optimal pH of the conditioned solution may be influenced by the properties of the protein, bioprocess, and/or other solution conditions selected for application of the methods. In addition, the time period for which the protein is incubated at a particular pH can also be optimized. The pH of the conditioned solution is typically determined according to the desired pH of the resulting polypeptide-containing solution after the incubation with the conditioned solution. In some embodiments, the pH is not adjusted and allowed to remain at approximately neutral pH (e.g., between 6 and 8). In certain other embodiments, the pH of the polypeptide-containing solution is adjusted to between about 4.0 and about 4.8. In other embodiments, the pH of the polypeptide-containing solution is adjusted to between about 3.0 and 4.0. In other embodiments, the pH of the polypeptide-containing solution is adjusted to between about 2.5 and 4.8. In yet other embodiments, the pH of the polypeptide-containing solution is adjusted to about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, or about 4.8. In certain other embodiments, the pH of the polypeptide-containing solution is adjusted to about 2.5 or lower. In yet other embodiments, the pH polypeptide-containing solution is adjusted to about 4.8 or higher. Additional non-limiting examples of such test studies and experiments are disclosed in Example 10 and Table 3.

Gas Identity and Dissolved Gas Levels

In another aspect of the methods, one predetermined solution parameter is the identity of the gas added to the conditioned solution. According to the disclosed methods, a gas may be present or absent in the conditioned solution depending on the desired disulfide bond formation result for the specific protein and/or bioprocess. In the embodiments where a gas is present in the conditioned solution, one or more specific gasses are selected for inclusion in the conditioned solution. Examples of gasses that can be selected are oxygen ($O_2$), carbon dioxide ($CO_2$), nitrogen (N), and different compositions of mixed gasses, such as 20% $O_2$/10% $CO_2$/70% air or 20% $O_2$5% $CO_2$/75% air.

In certain embodiments of the disclosed methods where a gas is present in the conditioned solution, another predetermined solution parameter is the dissolved gas level in the conditioned solution. A range of dissolved gas levels of the selected gas or gasses can be used according to the methods disclosed. Once a gas is selected, the gas concentration must be optimized according to the selected gas, protein, and/or bioprocess.

Conductivity

In another aspect of the methods, one predetermined solution parameter is the conductivity of the conditioned solution. According to the disclosed methods, conductivity may be set to a desired level depending on the desired disulfide bond formation result for the specific protein and/or bioprocess. Conductivity can be controlled via the addition of salts, such as sodium chloride, potassium chloride, ammonium sulfate, sodium phosphate, or other chemicals known in the art to modify the conductivity of a solution. Additionally, certain stages within the bioprocess may be selected as half antibody control points according to their typical conductivity. For example, a cell culture process is typically performed at physiological conductivity (10-15 mS/cm) while an ion exchange load material is typically low in conductivity (<10 mS/cm).

Viable Cell Density

In another aspect of the methods, one predetermined solution parameter is the viable cell density of the conditioned solution. In certain embodiments, a bioreactor unit operation is terminated at a specific day in the bioreactor campaign that has been matched to a designated viable cell density. According to the disclosed methods, viable cells may be present or absent in the conditioned solution depending on the desired disulfide bond formation result for the specific protein and/or bioprocess. In certain embodiments, the viable cell density is at least about $2 \times 10^6$ cells/mL.

Cell-Containing Methods

In one aspect, the disclosed methods can be applied at a time point in the bioprocess when the protein or polypeptides are in a solution comprising a plurality of cells (also referred to as a "cell-containing solution", "cell-containing suspension", or "unclarified harvest"). For typical bioprocesses used in protein production, the protein of interest is present in a solution comprising a plurality of cells at certain time points during the bioprocess. At these time points, the protein may be present in several possible bioprocess locations, including for example a bioreactor, holding tank, or a non-bioreactor unit operation vessel comprising a plurality of cells. Unclarified harvest may be obtained from such bioreactor processes as fed-batch, batch, or perfusion (continuous) processes. In some embodiments, the methods can be applied in a vessel separate from the bioreactor. In yet other embodiments, the methods can be applied within a unit operation vessel designed specifically to achieve the desired disulfide bond formation using a specific conditioned solution. For example, the unit operation vessel can be designed to achieve desired conversion of half antibody to full antibody under specified conditions. Non-limiting examples of these separate vessels include a tubular reactor, continuous stirred-tank reactor (CSTR), and a recirculation loop. Additional information regarding these bioprocess locations is provided elsewhere in the specification.

In some embodiments of the methods where the protein of interest is present in a solution comprising a plurality of cells, the protein is contacted with a conditioned solution that includes a population of viable cells. In certain of these embodiments, the conditioned solution may be the same solution that comprises the protein and plurality of cells. For example, if the disclosed methods are applied to a protein present in a bioreactor, the solution in the bioreactor (e.g. culture media) would be considered the conditioned solution, which comprises viable cells. As such, in this illustrative example, the predetermined solution parameters would correspond to the parameters of the solution already containing the protein of interest. In other such embodiments, the method comprises incubation of the protein with a conditioned solution that is obtained from the bioprocess, such as for example a solution comprising viable cells obtained at the conclusion of a fed-batch or batch bioreactor campaign. In some embodiments, the disclosed methods are applied at the conclusion of a fed-batch or batch bioreactor campaign and before the clarification or capture steps of a protein production bioprocess. However, depending on the particular protein, bioprocess, and desired disulfide bond formation result, the "hold" step can be implemented at virtually any stage of the protein production bioprocess, depending on considerations such as time required to achieve the disulfide bond formation result, cost of reagents, and/or ease of implementation.

In certain embodiments, the disclosed method comprises a step where the cell-containing solution comprising the protein undergoes a "hold" for a certain predetermined time. This "hold" step is an unconventional step in a typical protein production bioprocess. As illustrated in the examples, depending on the test conditions and conditioned solution parameters, holding a biotherapeutic IgG4 antibody in the presence of cells is surprisingly able to decrease, increase, or approximately maintain the proportion of half antibody present in the antibody population (see, for example, FIG. 3 and Examples 1 through 7). Therefore, by incubating the conditioned solution comprising viable cells with the polypeptides for a predetermined time, the formation of disulfide bonds between polypeptides can be controlled.

In certain embodiments, no controlled feeding is used during the "hold" step. In another embodiment, for an even more streamlined process, the bioreactor itself could be used as the hold vessel and the typical bioreactor controls or feeds intended to maintain cell viability could be turned off. If the hold step is conducted in a bioreactor, controlled feeding can be ongoing, changed, or halted during the incubation hold time. In certain embodiments, the conditions during the "hold" step of the methods are not monitored and adjusted as rigorously as in the bioreactor. For example, in some such embodiments, the oxygen levels and pH parameters of the "held" antibody sample are only minimally or not monitored and adjusted in a manner designed to maintain or control cell viability or productivity.

In other embodiments, the conditions during the "hold" step of the methods are actively monitored and adjusted. For example, in some such embodiments, the oxygen levels and pH parameters of the "held" antibody sample are actively and tightly monitored and adjusted. Active monitoring and adjusting of the conditioned solution conditions during the hold step can occur during the full duration of the hold step, a part of the duration of the hold step, or none of the duration of the hold step. Active monitoring and adjusting of the conditioned solution during the hold step may be applied to ensure the reproducibility of the desired result on the antibody sample, even if this active monitoring and adjusting may not be necessary to achieve the desired disulfide bond formation results. This method comprising a hold step has been demonstrated at multiple scales using a variety of conditions, solutions, and configurations as disclosed herein. The unit operation of holding a solution containing the multimeric protein (e.g. the "hold" step of the disclosed methods) can be performed using at least one reservoir. The volume of the reservoir can vary over a wide range depending on the bioprocess used for producing the protein. For example, the reservoir that can be used to achieve this unit operation can have a volume of about 1 mL to about 20,000 L, such as in commercial production bioprocesses. The reservoir can hold the fluid containing the antibody for a wide range of time periods, ranging from about 1 minute up to 3 weeks or longer in certain production design embodiments. The reservoir can be used to both hold and refrigerate (e.g., at a temperature of less than 25° C., less than 15° C., or less than 10° C.) or hold and heat (e.g. at temperature greater than 25° C., greater than 30° C. or greater than 35° C.) the solution containing the antibody. The reservoir can have any shape, including a circular cylinder, an oval cylinder, or an approximately rectangular sealed and nonpermeable bag.

Different incubation conditions in the unclarified harvest hold have been shown to lead to different outcomes. In one aspect, the most significant preconditioned solution parameters for the cell-containing protein solutions include hold time, hold temperature, cell viability at harvest (as controlled by harvest day), and agitation (See FIGS. 3-4). In one exemplary embodiment, cell-containing (unclarified) harvest can be collected and chilled to 8° C. for 10 or more days before subsequent processing in clarification and capture downstream steps.

Figure 5:
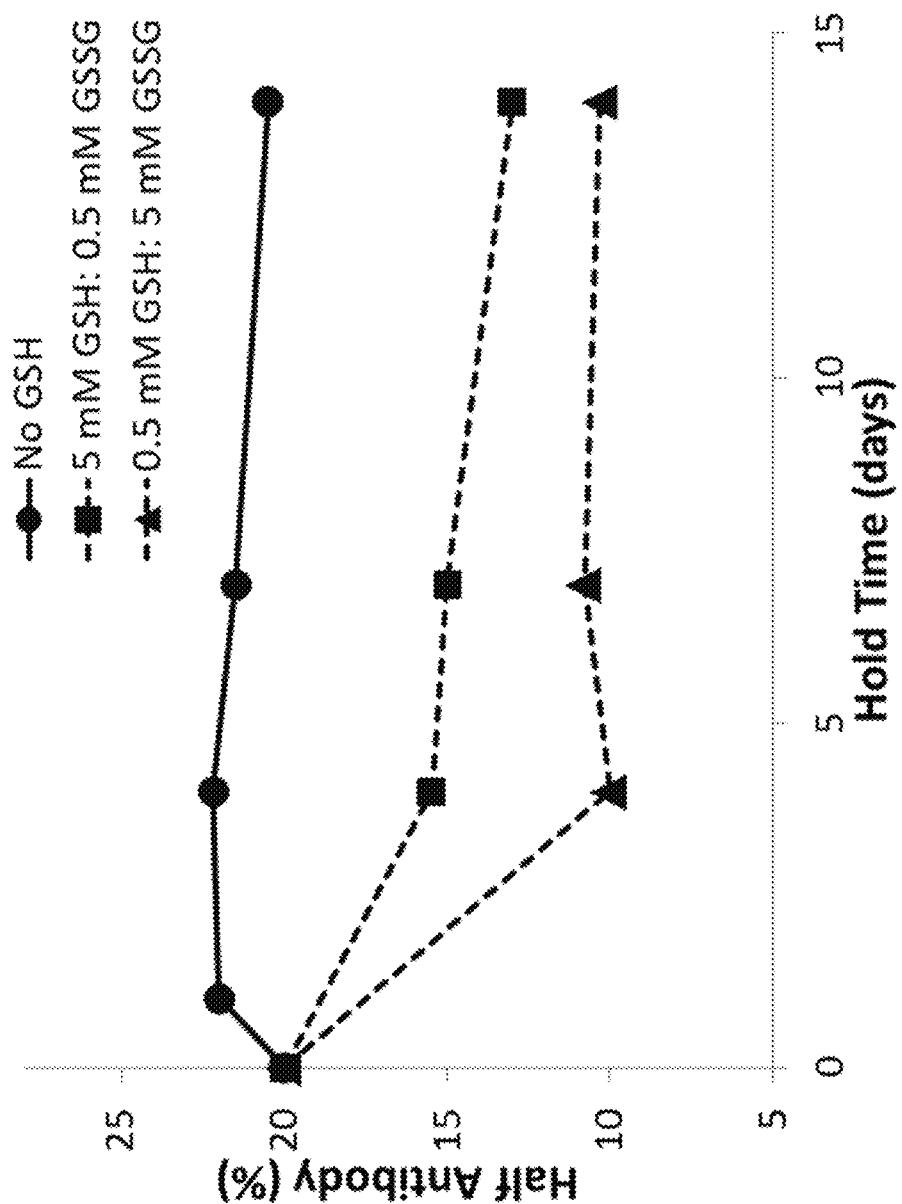
FIG. 5 depicts the effect of adding a redox reagent in the cell-containing (unclarified harvest) hold study. Half antibody content in percentage of total antibody molecules is shown as a function of hold time (in days) as a function of no glutathione addition (circles), addition of 5 mM reduced glutathione (GSH) and 0.5 mM oxidized glutathione (GSSG, squares), or addition of 0.5 mM GSH and 5 mM GSSG (triangles). Samples were held for specified times at 8° C. Initial cell viability for all three conditions was approximately $2.5 \times 10^6$ cells/mL.

Further, as disclosed above, the methods provided herein disclose the addition of redox reagents to the cell-containing protein solutions in order to accelerate the formation of disulfide bonds between polypeptides. For example, as observed by the conversion of half antibody to full antibody, cell-containing protein solutions comprising redox reagents may decrease the proportion of Hab at a more rapid rate and to a greater degree than unclarified harvest samples without redox reagent (FIG. 5). In one embodiment, in order to decrease the level of half antibody, a cocktail of redox reagents, such as for example 0.5 mM reduced glutathione and 5 mM oxidized glutathione, could be added to the cell-containing harvest, for days instead of weeks, before subsequent processing downstream.

Cell-Free Methods

In another aspect, the disclosed methods can be applied at a time point in the bioprocess, bioprocess step, or unit operation when the polypeptides are in a "cell-free" solution. These cell free solutions comprise the protein of interest, but essentially no cells are present in the solution. The lower level of heterogeneity and complexity in these cell-free solutions is advantageous for application of the methods disclosed herein. In certain embodiments, the cell-free solution comprises a Protein A eluate. In other embodiments, the cell-free solution comprises clarified harvest. Other solutions, buffers, and/or eluates can be used in the cell-free solution according to the methods described herein.

For typical bioprocesses used in protein production, the protein of interest is present in a "cell-free" solution at certain time points in the bioprocess, bioprocess step, or unit operation. In certain exemplary embodiments, the disclosed methods are applied at a time point during the bioprocess step of viral inactivation, adjustment, chromatography, filtration, dilution, concentration, or any other bioprocess step that is cell-free. (FIG. 2). Additional non-limiting examples of steps during the bioprocess where the protein solution can be cell-free include, but are not limited to, clarified harvest, capture eluate, intermediate chromatography process intermediates, or polishing chromatography process intermediates. (FIG. 2). There are many opportunities to apply the disclosed methods throughout a bioprocess, which typically includes steps in which solution phase conditions are actively manipulated, including for example when pH is lowered to achieve viral inactivation or when pH or conductivity is adjusted before or after a chromatography column operation. In certain embodiments, the disclosed methods would be applied at the clarified harvest stage. In certain other embodiments, the disclosed methods would be applied at the capture eluate stage. In some embodiments, the cell-free solution is a post-capture solution.

As disclosed herein, the optimal incubation conditions and predetermined condition parameters for the cell-free solution methods should first be determined for the specific protein of interest. The effect of incubation conditions and predetermined condition parameters on disulfide bond formation can be demonstrated by measuring the proportion of half antibody (for example, IgG4 half antibody) present in the protein solution. In some embodiments, redox reagents can be added to a cell-free solution, such as a process intermediate, to rapidly increase the disulfide bond formation between polypeptides of a multimeric protein. Using the methods disclosed herein, by measuring the proportion of IgG4 half antibody in a cell-free protein solution, the disulfide bonds between polypeptides can be effectively controlled by addition of certain redox reagents at specified concentrations, including for example 2-MEA. For example, studies to optimize the incubation conditions and predetermined condition parameters to decrease half antibody were performed, evaluating exemplary conditions such as pH, time, temperature, concentration of redox reagent, and concentration of IgG4 antibody. See, e.g., Examples 9 through 15. In one such exemplary study, when clarified harvest comprising the IgG4 antibody was incubated with the redox reagent 2-mercaptoethylamine (2-MEA) at 2-8° C. and purified on a Protein A column to remove the redox reagent, the proportion of Hab was decreased from about 18% to about 9% within 1 hour and, under certain conditions, in as little as 10 minutes. (See, e.g. FIG. 9). In certain embodiments, the redox reagent used in the disclosed methods is 2-MEA. 2-MEA was shown to be the most effective redox reagent for reducing Hab content in the tested exemplary antibody solutions. In certain embodiments, the formation of disulfide bonds between polypeptides in cell-free solutions is highly dependent on the pH of the conditioned solution.

Definitions

As used herein, the word "a" before a noun represents one or more of the particular noun. For example, the phrase "an antibody" represents "one or more antibodies."

The term "antibody," as used herein, broadly refers to any immunoglobulin (Ig) molecule comprised of four polypeptide chains, two heavy (H) chains and two light (L) chains, or any functional mutant, variant, or derivation thereof, which retains the essential epitope binding features of an immunoglobulin (Ig) molecule. In most antibodies, each heavy chain is comprised of a heavy chain variable region (abbreviated herein as HCVR or VH) and a heavy chain constant region. The heavy chain constant region is comprised of three domains, CH1, CH2, and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The antibody may also be a bi-specific antibody, tri-specific antibody, a dimer antibody, trimer antibody, or multimer antibody. (See, e.g., U.S. Patent Application Publication No. US20120251541 A1).

The term "antibody fragment" as used herein, refers to a portion of a full antibody, and is typically one polypeptide chain (either a heavy (H) chain or light (L) chain) which retains the essential epitope binding features of an Ig molecule, or any functional mutant, variant, or derivation thereof. Examples of antibody fragments include, but are not limited to, $F_{ab}$, $F_{ab'}$, $F_{(ab')2}$ and $F_v$ fragments, functional heavy chain fragments, functional light chain fragments, Affibodies®, and Nanobodies®.

A "humanized antibody" is an antibody that is derived from a non-human species, in which certain amino acids in the framework and constant domains of the heavy and light chains have been mutated so as to avoid or abrogate an immune response in humans. Humanized forms of non-human (for instance murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody typically also will comprise at least a portion of an immunoglobulin constant region (Fc), typically that of a human immunoglobulin. For further details, see Jones et al., 1986, Nature 321:522-525; Riechmann et al., 1988, Nature 332:323-329; Presta et al., 1992, Curr. Op. Struct. Biol. 2:593-596.

Non-limiting examples of therapeutic antibodies include: panitumumab, omalizumab, abagovomab, abciximab, actoxumab, adalimumab, adecatumumab, afelimomab, afutuzumab, alacizumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, etanercept, golimumab, infliximab, natalizumab, palivizumab, panitumumab, pertuzumab, ranibizumab, rituximab, tocilizumab, and trastuzumab.

The term "non-antibody protein" as used herein is any protein that is unable to be bound through any one of the following immunoglobulin-specific affinity interactions: Protein A binding to the Fc-region, Protein G binding to the Fab-region, Protein G binding to the Fc-region, or Protein L binding to the immunoglobulin light chain. In certain embodiments, the non-antibody protein is a biotherapeutic protein. The biotherapeutic protein can be, e.g., an engineered protein, enzyme, hormone, hematological factor, growth factor, or immunological factor. The term "non-antibody protein" can refer to the protein product at any stage of a bioprocess, including before, during, or after a purification stage. A non-antibody protein is a recombinant protein that is purified and/or isolated from a heterogeneous solution comprising the non-antibody protein and other components. Examples of such components are contaminating proteins, lipids, and nucleic acids present in a liquid culture medium or from a host cell (e.g., from a mammalian, yeast, or bacterial host cell) and other biological contaminants (e.g., viral and bacterial contaminants).

The term "multimeric protein" is defined herein to include proteins comprising one or more polypeptides that are associated, or joined, by one or more disulfide bonds. A multimeric protein can exist as a complex of more than one polypeptide monomer sub-unit in which each monomer sub-unit is associated with one or more other monomer sub-units by one or more disulfide bonds. A multimeric protein may comprise two or more identical polypeptide chains while not containing any different polypeptide chains ("homomultimeric"). A "homomultimer" consists of two or more copies of the same polypeptide chain. Similarly, a "homodimer" consists of two copies of the same polypeptide chain, a "homotrimer" consists of three copies of the same polypeptide chain, etc. Alternatively, a multimeric protein may comprise at least two different polypeptide chains. ("heteromultimeric"). If the heteromultimer has three or more polypeptide chains, some of them can be identical to each other as long as at least one is different from the others. The term "multimer" encompasses terms such as "dimer," "trimer," or "tetramer," which specify how many polypeptide chains the multimer contains. Antibodies are examples of multimeric proteins. Examples of antibody-like multimeric proteins include scFv, diabody, and tribody or triabody molecules, or multimers of Fc-fusion proteins. Examples of non-antibody proteins that may exist as multimeric proteins include fibrinogen, apolipoprotein heterodimers, platelet-derived growth factor, reelin, and porcine submaxillary mucin.

The term "polypeptide" as used herein means a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. The definition of "polypeptides" as used herein comprises both monomeric (e.g. monomers) and multimeric forms (e.g. dimers, trimers, etc.) of a protein. Fibrinogen is one example of a hexameric protein. Other examples of polypeptides include heavy chain and light chain antibody peptides.

The term "full antibody" includes antibodies in which the inter-heavy chain disulfide bond(s) are present, such that the full antibody is observed as combined two light chain polypeptides and two heavy chain polypeptides using non-reduced sodium dodecyl sulfate-poly acrylamide gel electrophoresis or other analytical techniques using non-reduced, denaturing solution conditions. (See, e.g., FIG. 11 and FIG. 12).

Figure 1:
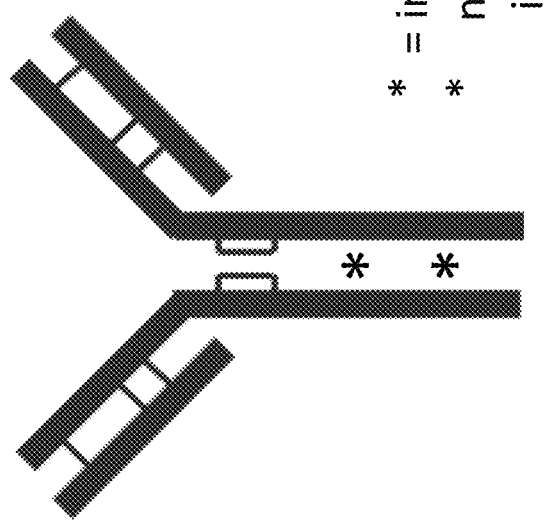
FIG. 1: Schematic representations of exemplary multimeric proteins to which the biomanufacturing method for control of disulfide bond formation can be applied.
Figure 1:
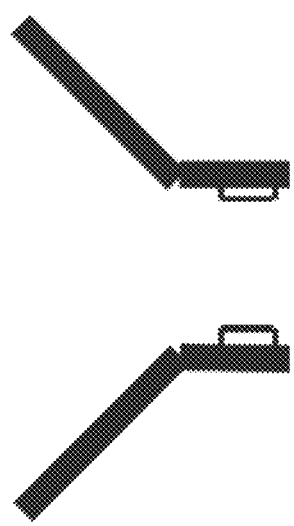
Figure 1:
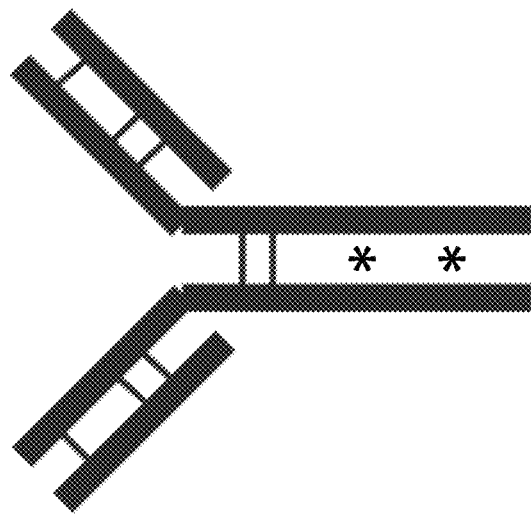

The term "half-antibody" includes antibodies (e.g. IgG4 antibodies) in which, the inter-heavy chain disulfide bond(s) are absent, such that the half antibody is observed as a combined single light chain polypeptide and single heavy chain polypeptide using non-reduced sodium dodecyl sulfate-poly acrylamide gel electrophoresis or other analytical techniques using non-reduced, denaturing solution conditions. Under non-denaturing conditions, half-antibodies are difficult to detect due to strong interchain non-covalent interactions still prevalent in the absence of interchain disulfide bonds. (Taylor et al., 2006, *Anal Biochem.* 353(2): 204-208). Half antibodies are illustrated in FIG. 1, row A and the results of non-reduced sodium dodecyl sulfate-poly acrylamide gel electrophoresis analysis of a half antibody containing sample are included in FIG. 12.

The term "half antibody conversion" or "conversion of half antibody" as used herein refers to a biochemical process by which a half antibody becomes a full antibody, for example, by formation or reformation of interchain disulfide bonds.

The term "activity" includes activities such as the binding specificity and affinity of an antibody or half antibody for one or more antigens, targets, or ligands.

The term "IgG4" includes a subclass of IgG immunoglobulins that are produced during a secondary immune response and are most commonly found in the blood. These IgG antibodies typically contain the γ4 heavy chain.

The methods disclosed herein provide significant benefits to IgG4 antibodies, particularly therapeutic IgG4 antibodies. Non-limiting examples of IgG4 antibodies that can be produced by the methods provided herein include natalizumab (Tysabri®, Biogen Idec), gemtuzumab (Mylotarg®, Pfizer), and fresolimumab (Genzyme). Natalizumab, which is directed to the α4 subunit of α4β1 (VLA-4) and α4β7 integrins, and gemtuzumab which is specific for CD33, are two humanized IgG4 antibodies previously approved for human use. Natalizumab is effective in the treatment of multiple sclerosis (MS), and gemtuzumab, conjugated to a cytotoxic calicheamicin derivative, is used to treat Acute Myeloid Leukemia (AML) (Zohren et al., 2008, *Blood* 111:3893-3895). Development of another humanized IgG4-based therapeutic, TGN1412 (CD28-specific), was discontinued after causing unforeseen adverse events in healthy individuals. Natalizumab has also been associated with adverse events, in particular progressive multifocal leukoencephalopathy, a central nervous system (CNS) infection with the JC polyoma virus.

The term "half-molecule exchange" refers to a type of protein modification for an antibody, such as an IgG4, in which an antibody heavy chain and attached light chain (half-molecule) is swapped for a heavy-light chain pair from another IgG4 molecule. Thus, an antibody molecule may acquire two distinct Fab arms recognizing two distinct antigens (resulting in bispecific molecules) while their Fc domain structure remains unchanged. (Labrijn et al., 2013, *Proc Natl Acad Sci USA.* 110(13):5145-50). Inter-species half-molecule exchange may also occur resulting in altered Fc domain structure, as well, comprising domains from each of the two species contributors. (Labrijn et al., 2009, *Nature Biotechnol.* 27(8):767-771). A half-molecule exchange is also referred to as a "Fab arm exchange." (Rispens et al., 2011, *J Am Chem Soc.* 133(26):10302-10311).

The term "non-reducing" refers to conditions under which disulfide-bonds (e.g., disulfide linkage(s)) are preserved. Specifically, conditions under which disulfide bonds remain intact and are not converted to free sulfhydrils.

The term "substantially free" means a composition (e.g., a liquid culture medium) that is at least or about 90% free (e.g., at least or about 95%, 96%, 97%, 98%, or at least or about 99% free, or about 100% free) of a specified substance.

The term "culturing" or "cell culturing" means the maintenance or proliferation of a cell under a controlled set of physical conditions.

The term "continuous process" means a process that continuously achieves or produces a result (e.g., a process which continuously produces a therapeutic protein drug substance from a liquid culture medium). For example, a therapeutic antibody drug substance is continuously produced while the systems are in operation (accounting, of course, for an initial lag period while the antibody travels through the system to the exit port). (See, generally, Shuler et al., 1992. *Bioprocess engineering: basic concepts*. New York: Prentice-Hall.) One exemplary continuous biological manufacturing system is described in International Patent Application No. PCT/US2014/019909.

The term "semi-continuous process" means a process that is a generally continuous process for purifying a target molecule, where input of the fluid material in any single process step or the output is discontinuous or intermittent. For example, the input in a process step (e.g., a bind and elute chromatography step) may be loaded continuously; however, the output may be collected intermittently, where the other process steps in the purification process are continuous. Accordingly, in some embodiments, the processes described herein are "semi-continuous", in that they include at least one unit operation which is operated in an intermittent matter, whereas the other unit operations in the process or system may be operated in a continuous manner.

The term "recover" or "recovering" means a step performed to partially purify or isolate (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight a protein from one or more other components present in a liquid culture medium or a diluted liquid culture medium (e.g., culture medium proteins or one or more other components (e.g., DNA, RNA, or other proteins) present in or secreted from a mammalian cell). Typically, capturing is performed using a resin that binds a protein (e.g., through the use of affinity chromatography). Non-limiting methods for capturing a protein from a liquid culture medium or diluted liquid culture medium are described herein and others are known in the art. A protein can be recovered from a liquid culture medium using a chromatography column or chromatographic membrane (e.g., any of the chromatography columns or chromatographic membranes described herein).

The term "purifying" means a step performed to isolate an antibody from one or more other components present in a fluid containing an antibody (e.g., liquid culture medium proteins or one or more other components (e.g., DNA, RNA, or other proteins) present in or secreted from a mammalian cell). For example, purifying can be performed after an initial capturing step. Purifying can be performed using a resin that binds an antibody (e.g., through the use of affinity chromatography, anion or cation exchange chromatography, or molecular sieve chromatography). An antibody can be polished from a fluid containing the protein using a chromatography column or chromatographic membrane (e.g., any of the chromatography columns or chromatographic membranes described herein).

The term "eluate" is a term of art and means a fluid that is emitted from a chromatography column or chromatographic membrane that contains a detectable amount of an antibody. One non-limiting example is Protein A eluate.

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

The term "clarifying" means the removal of cells, cell debris, and other large bioreactor or cell culture impurities from a liquid (e.g. a liquid culture medium). Several methods of clarifying a protein sample are known in the art. Non-limiting examples of clarification methods include centrifugation, microfiltration, depth filtration, sterile filtration, precipitation, flocculation, and liquid-liquid extraction. The solution obtained immediately after completion of a clarification step is typically referred to as the "clarified harvest". Due to the clarification procedure, the clarified harvest is essentially cell-free.

The term "adjustment step" means a step within a bioprocess wherein one fluid containing the polypeptide is combined with one or more additional fluids in order to alter the parameters of the polypeptide-containing fluid, such as redox reagent concentration, pH, dissolved gas levels, conductivity, and/or viable cell density. Non-limiting examples of adjustment methods include addition of a low or high pH solution in order to decrease or increase pH, respectively, addition of a concentrate to increase conductivity or redox reagent concentration, or addition of a cell-containing fluid to a cell-free fluid. Methods of fluid addition include direct addition into a hold vessel, such as a tank or bag, or inline addition in which two or more fluids are combined with one another within a process flow. In certain embodiments, the adjustment step is performed using a buffer adjustment reservoir.

The term "perfusion bioreactor" means a bioreactor containing a plurality of cells in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some examples, there is an incremental change (e.g., increase or decrease) in the volume of the first liquid culture medium removed and added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "fed-batch bioreactor" is a term of art and means a bioreactor containing a plurality of cells in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder.

The term "bioprocess", as used herein, generally refers to any process applied to a protein according to the disclosed methods. In certain embodiments, the bioprocess is one or more functional steps ("unit operations") that can be performed in a process of manufacturing a therapeutic protein drug substance from a liquid culture medium. An example of a typical bioprocess is shown in FIG. 2. Non-limiting examples of a bioprocess include filtering (e.g., removal of contaminant bacteria, yeast viruses, or mycobacteria, and/or particular matter from a fluid containing an antibody), capturing, epitope tag removal, purifying, holding or storing, polishing, viral inactivating, adjusting the ionic concentration and/or pH of a fluid containing the antibody, and removing unwanted salts. In certain embodiments, the bioprocess is a bioreactor process, seed train, capture chromatography, intermediate chromatography, filtration, centrifugation, precipitation, flocculation, UV irradiation, and/or viral inactivation. In certain embodiments, the bioprocess occurs within a bioreactor or chromatography apparatus.

In some embodiments, the term "monitoring" refers to the ability to measure specific process parameters or process outputs such as product quality attributes (including half antibody level), pH, dissolved oxygen, media components, bioprocess unit operations, and flow rate. Monitoring can be applied according to the particular design of the experiment or bioprocess. For example, monitoring can be applied at one or more specific points in the bioprocess, for certain steps or time periods within the bioprocess, or for the duration of the bioprocess.

In some embodiments, the term "controlling" as used herein refers to the ability to change the formation or number of disulfide bonds between polypeptides of a multimeric protein by adjusting one or more incubation conditions and/or predetermined solution parameters. "Controlling" also refers to the ability to increase, decrease, or maintain the formation or number of disulfide bonds between polypeptides of a multimeric protein during a specific time point of a bioprocess. In some embodiments, the term "controlling" refers to the ability to change the level of half antibody present in the IgG4 antibody within a particular step or stage of the bioprocess or unit operation. Non-limiting examples of such parameters that may be adjusted include time, temperature, pH, redox reagent identity and concentration, gas identity, dissolved gas levels, conductivity, and/or viable cell density.

As used herein, the term "critical quality attribute", also referred to as "CQA", means a physical, chemical, biological, or microbiological property or characteristic that should be within an appropriate limit, range, or distribution to ensure the desired product quality. One example of a CQA is the number of disulfide bonds between polypeptides of a multimeric protein. Another example of a CQA is the proportion of half antibody in an antibody solution. Other non-limiting examples of CQAs include product purity, potency, charged isoform profile, post-translational modifications, oxidation, reductions, deamidation, adduct formation, clipped forms, enzymatic cleavage, specific activity, peptide map, dimer content, product aggregation, site specific glycosylation, total glycans, and/or glycosylation profile. The selection of appropriate CQAs and appropriate assays for specific applications of the disclosed methods are within the capabilities of one of ordinary skill in the art.

In certain embodiments, a CQA of an antibody is determined by measurement. In some such embodiments, a CQA is measured using a high-throughput and/or rapid analytical technique. In certain embodiments, a CQA is measured using an analytical technique comprising the following non-limiting examples: high-performance liquid chromatography (HPLC), differential refractometry, fluorescence, ultra-performance liquid chromatography (UPLC), multi-angle laser light scattering analysis (MALLS), mass spectroscopy, tandem mass spectroscopy, isoelectric focusing, SDS-PAGE, and/or differential scanning calorimetry. In yet other embodiments, the high-throughput and/or rapid analytical technique is performed by a robot. In further embodiments, the robot is a liquid-handling robot.

Chromatography

Protein production bioprocesses as described herein often involve the use of one or more chromatography columns. One or more different types of buffer can be employed during chromatography. As is known in the art, the one or more types of buffer used in the in the processes described herein will depend on the resin present in the chromatography column or the chromatographic membrane of the chromatography column, the protein of interest, and unit operation. For example, the volume and type(s) of buffer employed during the use of the chromatography column in any of the processes described herein can be chosen in order to optimize one or more CQAs or one or more of the following protein properties: the overall yield of protein, the activity of the protein, the level of purity of the antibody, and the removal of biological contaminants from a fluid containing the protein (e.g., absence of active viruses, mycobacteria, yeast, bacteria, or mammalian cells).

The unit operations that can be performed in the presently described bioprocesses include, for example, clarifying the protein, capturing the protein, inactivating viruses present in a fluid containing the protein, purifying the protein, holding a fluid containing the protein, holding a fluid containing the protein and cells, filtering or removing particulate material and/or cells from a fluid containing the protein, and adjusting the ionic concentration and/or pH of a fluid containing the protein.

The unit operation of recovering can be performed using a chromatography column or chromatography resin, e.g., that utilizes a recovery mechanism. Non-limiting examples of recovery mechanisms include a protein A-binding recovery mechanism, an protein- or protein fragment-binding recovery mechanism, a substrate-binding recovery mechanism, an aptamer-binding recovery mechanism, a tag-binding recovery mechanism (e.g., poly-His tag-based recovery mechanism), and a cofactor-binding recovery mechanism. Capturing can also be performed using a resin that can be used to perform cation exchange or anion exchange chromatography, or molecular sieve chromatography. Non-limiting resins that can be used to recover a protein are described herein.

The unit operation of purifying a protein can be performed using a chromatography column or chromatographic membrane that contains a resin, e.g., that utilizes a recovery system. Non-limiting examples of recovery mechanisms include a protein A-binding recovery mechanism, an protein- or protein fragment-binding recovery mechanism, a substrate-binding recovery mechanism, an aptamer-binding recovery mechanism, a tag-binding recovery mechanism (e.g., poly-His tag-based recovery mechanism), and a cofactor-binding recovery mechanism. Purifying can also be performed using a resin that can be used to perform cation exchange or anion exchange chromatography, or molecular sieve chromatography. Non-limiting resins that can be used to purify a protein are described herein.

The unit operations of filtering a fluid containing the protein can be performed using a filter, or a chromatography column or chromatographic membrane that contains a molecule sieve resin. As is known in the art, a wide variety of submicron filters (e.g., a filter with a pore size of less than 1 µm, less than 0.5 µm, less than 0.3 µm, about 0.2 µm, less than 0.2 µm, less than 100 nm, less than 80 nm, less than 60 nm, less than 40 nm, less than 20 nm, or less than 10 nm) are available in the art that are capable of removing any precipitated material and/or cells (e.g., precipitated, unfolded protein; precipitated, unwanted host cell proteins; precipitated lipids; bacteria; yeast cells; fungal cells; mycobacteria; and/or mammalian cells). Filters having a pore size of about 0.2 µm or less than 0.2 µm are known to effectively remove bacteria from the fluid containing the protein. A chromatography column or a chromatographic membrane containing a molecular sieve resin can also be used to perform the unit operation of filtering a fluid containing a protein.

Culturing Methods

Some of the processes described herein further include a step of culturing cells that produce a multimeric protein or the polypeptide sub-units of a multimeric protein in a bioreactor (e.g., a perfusion or fed-batch bioreactor) that contains a liquid culture medium, wherein a volume of the liquid culture medium that is either cell-containing or substantially free of cells is continuously or periodically removed from the bioreactor. The bioreactor can have a volume of, e.g., between about 1 L to about 10,000 L (e.g., between about 1 L to about 50 L, between about 50 L to about 500 L, between about 500 L to about 1000 L, between 500 L to about 5000 L, between about 500 L to about 10,000 L, between about 5000 L to about 10,000 L, between about 1 L and about 10,000 L, between about 1 L and about 8,000 L, between about 1 L and about 6,000 L, between about 1 L and about 5,000 L, between about 100 L and about 5,000 L, between about 10 L and about 100 L, between about 10 L and about 4,000 L, between about 10 L and about 3,000 L, between about 10 L and about 2,000 L, or between about 10 L and about 1,000 L), or more. The amount of liquid culture medium present in a bioreactor can be, e.g., between about between about 0.5 L to about 5,000 L (e.g., between about 0.5 L to about 25 L, between about 25 L to about 250 L, between about 250 L to about 500 L, between 250 L to about 2500 L, between about 250 L to about 5,000 L, between about 2500 L to about 5,000 L, between about 0.5 L and about 5,000 L, between about 0.5 L and about 4,000 L, between about 0.5 L and about 3,000 L, between about 0.5 L and about 2,500 L, between about 50 L and about 2,500 L, between about 5 L and about 50 L, between about 5 L and about 2,000 L, between about 5 L and about 1,500 L, between about 5 L and about 1,000 L, or between about 5 L and about 500 L). Culturing cells can be performed, e.g., using a batch-feed bioreactor or a perfusion bioreactor. Non-limiting examples and different aspects of culturing cells are described below and can be used in any combination.

Cells

The cells that are cultured in some of the processes described herein can be bacteria (e.g., gram negative bacteria), yeast (e.g., *Saccharomyces cerevisiae, Pichia pastoris, Hansenula polymorpha, Kluyveromyces lactis, Schizosaccharomyces pombe, Yarrowia lipolytica,* or *Arxula adeninivorans*), or mammalian cells. The mammalian cell can be a cell that grows in suspension or an adherent cell. Non-limiting examples of mammalian cells that can be cultured in any of the processes described herein include: Chinese hamster ovary (CHO) cells (e.g., CHO DG44 cells or CHO-K1s cells), Sp2.0, myeloma cells (e.g., NS/0), B-cells, hybridoma cells, T-cells, human embryonic kidney (HEK) cells (e.g., HEK 293E and HEK 293F), African green monkey kidney epithelial cells (Vero) cells, and Madin-Darby Canine (Cocker Spaniel) kidney epithelial cells (MDCK) cells. In some examples where an adherent cell is cultured, the culture can also contain a plurality of microcarriers (e.g., microcarriers that contain one or more pores). Additional mammalian cells that can be cultured in any of the processes described herein are known in the art.

The mammalian cell can contain a recombinant nucleic acid (e.g., a nucleic acid stably integrated in the mammalian cell's genome) that encodes a protein. Non-limiting examples of recombinant nucleic acids that encode exemplary antibodies are described below, as are antibodies that can be produced using the methods described herein. In some instances, the mammalian cell that is cultured in a bioreactor (e.g., any of the bioreactors described herein) was derived from a larger culture.

A nucleic acid encoding a protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a protein is not stably integrated into a chromosome of the mammalian cell (transient transfection), while in others the nucleic acid is integrated. Alternatively or in addition, the nucleic acid encoding a protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A vector containing the nucleic acid can, if desired, also contain a selectable marker (e.g., a gene that confers hygromycin, puromycin, or neomycin resistance to the mammalian cell).

In some instances, the protein is a secreted protein and is released by the mammalian cell into the extracellular medium (e.g., the first and/or second liquid culture medium). For example, a nucleic acid sequence encoding a soluble protein can contain a sequence that encodes a secretion signal peptide at the N- or C-terminus of the protein, which is cleaved by an enzyme present in the mammalian cell, and subsequently released into the extracellular medium (e.g., the first and/or second liquid culture medium).

Culture Media

The liquid culture media (e.g., a first and/or second tissue culture medium) can be supplemented with a mammalian serum (e.g., fetal calf serum and bovine serum), and/or a growth hormone or growth factor (e.g., insulin, transferrin, and epidermal growth factor). Alternatively or in addition, the liquid culture media (e.g., a first and/or second liquid culture medium) can be a chemically-defined liquid culture medium, an animal-derived component free liquid culture medium, a serum-free liquid culture medium, or a serum-containing liquid culture medium. Non-limiting examples of chemically-defined liquid culture media, animal-derived component free liquid culture media, serum-free liquid culture media, and serum-containing liquid culture media are commercially available.

A liquid culture medium typically contains an energy source (e.g., a carbohydrate, such as glucose), essential amino acids (e.g., the basic set of twenty amino acids plus cysteine), vitamins and/or other organic compounds required at low concentrations, free fatty acids, and/or trace elements. The liquid culture media (e.g., a first and/or second liquid culture medium) can, if desired, be supplemented with, e.g., a mammalian hormone or growth factor (e.g., insulin, transferrin, or epidermal growth factor), salts and buffers (e.g., calcium, magnesium, and phosphate salts), nucleosides and bases (e.g., adenosine, thymidine, and hypoxanthine), protein and tissue hydrolysates, and/or any combination of these additives.

A wide variety of different liquid culture media that can be used to culture cells in any of the methods described herein are known in the art. Medium components that also may be useful in the present processes include, but are not limited to, redox reagents, chemically-defined (CD) hydrolysates, e.g., CD peptone, CD polypeptides (two or more amino acids), and CD growth factors. Additional examples of liquid tissue culture medium and medium components are known in the art. Skilled practitioners will appreciate that the first liquid culture medium and the second liquid culture medium described herein can be the same type of media or different media.

For bioprocesses used in protein production, the protein of interest (e.g. a multimeric protein) is present in a solution comprising a plurality of cells at certain time points during the bioprocess. During these time points, the protein may be present in several possible locations, including for example a bioreactor, holding tank, or a non-bioreactor unit operation vessel comprising a plurality of cells.

Fed-Batch Bioreactor

One non-limiting example of a bioreactor that can be used to culture the plurality of cells present in solution with the protein is a fed-batch bioreactor. Culturing a cell in a fed-batch bioreactor includes, over the majority of the culturing period, the addition (e.g., periodic or continuous addition) to the first liquid culture medium of a second volume of a second liquid culture medium. The adding of the second liquid culture medium can be performed continuously (e.g., at a rate that adds a volume of between 0.1% to 300% (e.g., between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours) or periodically (e.g., once every third day, once every other day, once a day, twice a day, three times a day, four times a day, or five times a day), or any combination thereof. Where performed periodically, the volume that is added (e.g., within about a 24-hour period, within an incremental time period of about 1 hour to about 24 hours, or within an incremental time period of greater than 24 hours) can be, e.g., between 0.1% to 300% (e.g., between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The use of fed-batch bioreactors to culture cells for protein production is well-described in the art.

Perfusion Bioreactor

The culturing step described herein can be performed using a perfusion bioreactor. Culturing a cell in a perfusion bioreactor includes the removal from the bioreactor of a first volume of a first liquid culture medium (e.g., containing any concentration of cells, e.g., a first volume of a first liquid culture medium that is substantially free of cells), and adding to the first liquid culture medium a second volume of a second liquid culture medium. Removal and adding can be performed simultaneously or sequentially, or a combination of the two. Further, removal and adding can be performed continuously or periodically, or any combination thereof. The first volume of the first liquid culture medium removed and the second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different. The use of perfusion bioreactors to culture cells for protein production is well-described in the art.

The interior surface of any of the bioreactors described herein may have at least one coating (e.g., at least one coating of gelatin, collagen, poly-L-ornithine, polystyrene, and laminin), and as is known in the art, one or more ports for the sparging of $O_2$, $CO_2$, and $N_2$ into the liquid culture medium, and a stir mechanism for agitating the liquid culture medium. The bioreactor can incubate the cell culture in a controlled humidified atmosphere (e.g., at a humidity of greater than 20%, 30%, 40%, 50%, 60%, 70%, 75%, 80%, 85%, 90%, or 95%, or a humidity of 100%). The bioreactor can also be equipped with a mechanical device that is capable of removing a volume of liquid culture medium from the bioreactor and optionally, a filter within the mechanical device that removes the cells from the liquid culture medium during the process of transfer of the liquid culture medium out of the bioreactor (e.g., an ATF system).

The concentration of protein in the solutions according to the claimed methods can be greater than about 1.0 mg/mL, greater than about 1.5 mg/mL, greater than about 2.0 mg/mL, greater than about 2.5 mg/mL, greater than about 3.0 mg/mL, greater than about 3.5 mg/mL, greater than about 4.0 mg/mL, greater than about 4.5 mg/mL, greater than about 5.0 mg/mL, greater than about 5.5 mg/mL, greater than about 6.0 mg/mL, greater than about 6.5 mg/mL, greater than about 7.0 mg/mL, greater than about 7.5 mg/mL, greater than about 8.0 mg/mL, greater than about 8.5 mg/mL, greater than about 9.0 mg/mL, greater than about 10.0 mg/mL, greater than about 12.5 mg/mL, or greater than about 15.0 mg/mL. In certain embodiments, the concentration of protein in the cell-containing solutions of the claimed methods is about 0.01 mg/mL to about 20 mg/mL. In other embodiments, the concentration of protein in the cell-free solutions of the claimed methods is about 0.1 mg/mL to about 100 mg/mL.

In general, the practice of the present invention employs, unless otherwise indicated, conventional techniques of chemistry, molecular biology, recombinant DNA technology, immunology (especially, e.g., immunoglobulin technology), and standard techniques in electrophoresis. See, e.g., Sambrook et al., 1989, *Molecular Cloning: A Laboratory Manual*, Cold Spring Harbor Laboratory Press; Paul, S. (ed.), 1995, *Antibody engineering protocols* (Vol. 51). Humana Press; McCafferty et al. (eds.), 1996, *Antibody engineering: a practical approach*, Practical Approach Series, 169, IRL press; Harlow et al. (eds.), 1999, Using Antibodies: A Laboratory Manual, Cold Spring Harbor Laboratory Press, NY; Ausubel et al., 2007, Current Protocols in Molecular Biology, John Wiley & Sons, NY; Bousse et al., 2001, *Anal. Chem.* 73:1207-1212; Knapp et al., 2001, Proceedings of the μTAS 2001 Symposium, *Micro Total Analysis Systems* 2001, 7-10, Kluwer Academic Publishers, Dordrecht, Netherlands; Mhatre et al., 1999, *Rapid Commun Mass Spectrom.* 13(24):2503-10. The techniques disclosed in these publications are incorporated by reference in their entirety.

Unless otherwise defined, all technical and scientific terms used herein have the same meaning as commonly understood by one of ordinary skill in the art to which this invention belongs. Scientific techniques and materials are described herein for use in the present invention; other, suitable techniques and materials can also be used. The materials, techniques, and examples are illustrative only and not intended to be limiting. All publications, patent applications, patents, sequences, database entries, and other references mentioned herein are incorporated by reference in their entirety. In case of conflict, the present specification, including definitions, will control.

The Examples that follow are illustrative of specific embodiments of the invention, and various uses thereof. They are set forth for explanatory purposes only, and should not be construed as limiting the scope of the invention in any way.

EXAMPLES

Example 1. Controlling the Proportion of IgG4 Half-Antibody: Evaluation of Unclarified Harvests Overall Approach The ability to control the level of IgG4 half antibody was studied in an unclarified cell culture harvest, which is a cell-containing system. In this example, unclarified harvest obtained upon termination of a fed-batch bioreactor campaign was subjected to a number of experimental conditions and monitored, as a function of time, for the percentage of half antibody (Hab) present in the IgG4 population. The key experimental conditions included the following: unclarified harvest hold time, hold temperature, and cell viability at harvest (as controlled by harvest day). Along with the half antibody level, the secondary experimental outputs included a number of solution phase parameters, such as pH, viable cell density, and dissolved gases.

Materials, Methods, and Analytical Techniques

In order to measure half antibody content, unclarified harvest sample purification was performed by 0.2 um filtration followed by purification on a Freedom EVO 150 Tecan liquid handler using PreDictor RoboColumns (200 uL) packed with MabSelect SuRe resin obtained from GE Life Sciences. Half antibody analysis was performed by non-reduced SDS-PAGE. SDS-PAGE under non-reducing conditions was performed according to standard techniques (e.g., see Sambrook et al., 1989; Ausubel et al., 2007). Staining of the gels was performed with Simply Blue SafeStain (Life Technologies, Cat #LC6065). The level of half-antibody was measured from the scanned gel image and quantified by a densitometer.

Unclarified Harvest Sample Preparation and Handling

Approximately 20 mL of unclarified harvest was distributed into multiple 20 mL PETG bottles with minimal headspace. The procedure for distributing the unclarified harvest into 20 mL samples was designed to ensure homogeneity and sterility in each sample by transferring unclarified harvest into a spinner flask which was continuously stirred while samples were obtained by sequential pipetting. Bottles were only opened once for analysis and/or purification. Particular care was made to control initial cell density during the distribution of the unclarified harvest samples. At designated time points, unclarified harvest samples were tested for solution-phase characteristics such as pH, dissolved gases, and viable cell density, followed by capture purification. The purified sample was then assayed for Hab content.

The results of the experiments presented in this example were also confirmed in 2 L and 5 L unclarified harvest samples, which were collected using a disposable bag. Therefore the methods disclosed herein can be scaled up to larger volumes of antibody production, such as in commercial production and/or manufacturing of the antibody.

Example 2. Hold Time: Unclarified Harvest

Several key variables were studied in the primary experimental study to demonstrate the ability to control the level of IgG4 half antibody present within an antibody sample. These key variables included unclarified harvest hold time, hold temperature, and initial viable cell density (as controlled by viability at harvest).

To establish a baseline half antibody proportion value for each experiment, the half antibody content was measured in an antibody sample prepared using a traditional protocol, which consisted of a hold time of 0 minutes (e.g. no hold step) and did not adjust any other conditions according to the methods disclosed herein. The half antibody content of this purified sample was, on average, about 21% (as measured by non-reduced SDS PAGE).

Unclarified harvest fluid was obtained from fed-batch cultures of a therapeutic IgG4 molecule. Cell culture was performed in 15 L Broadley James glass vessels with Delta V control. Throughout the unclarified harvest sample hold period, viable cell density and percent viability were measured using a Vi-Cell Cell Viability Analyzer (Beckman Coulter), and pH, $pCO_2$ and $pO_2$ were measured using a Blood Gas Analyzer (Siemens).

Depending on the test conditions, holding the biotherapeutic IgG4 in the presence of cells was able to decrease, increase, or approximately maintain the level of half antibody present within the antibody population. The results of these experiments are shown in FIG. 3.

Example 3. Initial Viable Cell Density: Unclarified Harvest

The second major experimental variable or control parameter tested in this study was the initial viable cell density (FIG. 3, graphs B and D).

Bioreactor samples were taken at two different harvest days, representing approximately 70% and 35% cell viability. In this experiment the initial viable cell density was evaluated at $4.5 \times 10^6$ cells/mL (earlier harvest day from the fed-batch reactor) or $2.5 \times 10^6$ cells/mL (later harvest day from the fed-batch reactor). The hold temperature was held constant between the two test cell density conditions at 8° C. In this experiment, the half antibody level did not decrease for the 8° C. sample with the comparatively lower initial viable cell density of $2.5 \times 10^6$ cells/mL.

Upon closer analysis, it was observed that once the viable cell density measurement decreased to approximately $2 \times 10^6$ cells/mL, no further decreases in half antibody were realized in either experimental test condition (FIG. 3). This phenomenon was observed in both samples with different initial viable cell densities. The strong dependence of Hab conversion on viable cell density was observed throughout the data set and the results presented in FIG. 3, graphs B and D are meant to be representative.

Example 4. Hold Temperature: Unclarified Harvest

Unclarified harvest was held at three different temperatures: 2-10° C. (cold room), 20-22° C. (ambient temperature), and 37° C. (warm room).

Several potential control parameters emerged from an analysis of the experimental results. The half antibody content was found to be significantly affected by the presence of viable cells in the unclarified harvest.

In FIG. 3, graph A, the most dramatic decrease in half antibody was observed for the cold temperature (8° C.) hold condition, which corresponded to the highest level of viable cell density that was evaluated in this study. The half antibody trend at the warm condition (37° C.) included both an immediate decrease from 21% to 19% and, ultimately, an increase to a final half antibody level of about 25%. The change in the half antibody progression at 37° C. from decreasing to increasing corresponded directly to the point at which all cells present in the sample were no longer viable (FIG. 3, graph B), another indication of the important role of viable cells in the half antibody control process.

Thus, the impact of elevated temperature in the cell-containing (unclarified) harvest hold condition indicated a control parameter by which the level of half antibody could be increased.

Example 5. Agitation During Hold: Unclarified Harvest

In addition to variations in hold temperature, the effect of mixing or agitation was tested by placing selected samples of unclarified harvest on a rotator during the hold period, and other samples remained still (static) throughout the hold.

Figure 4:
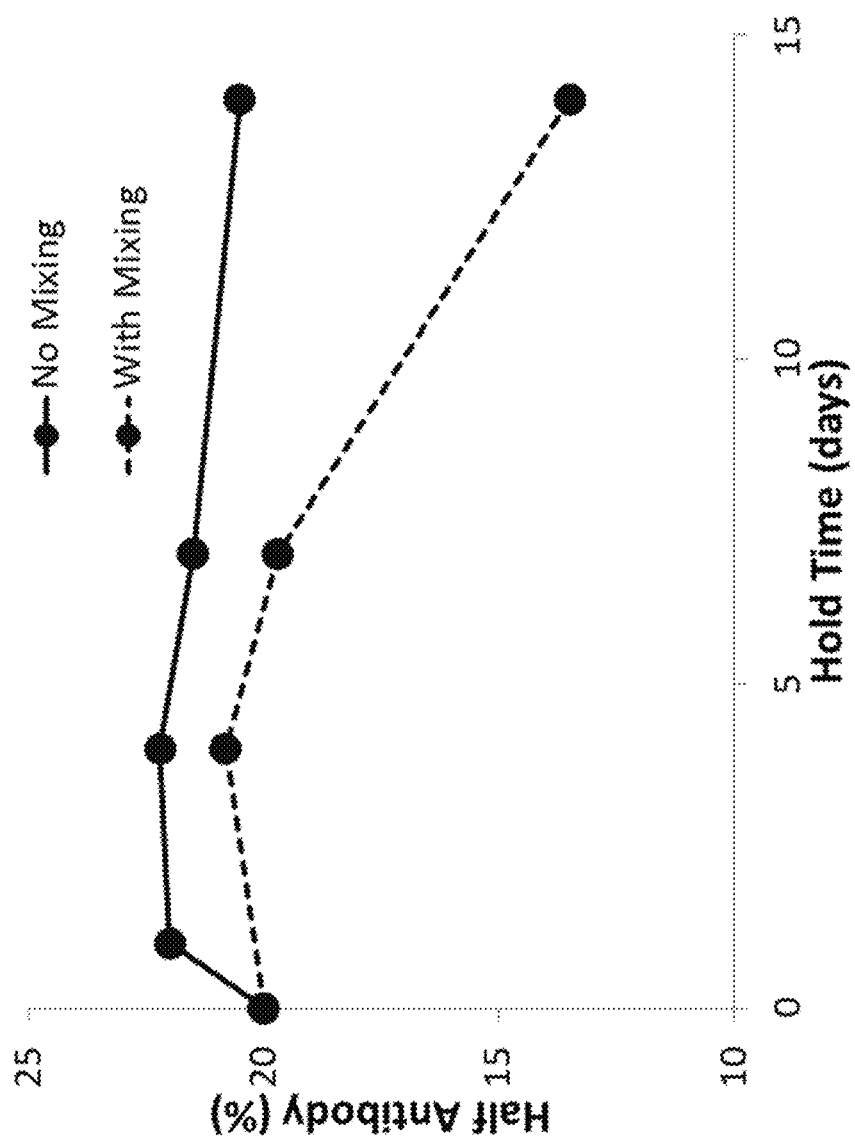
FIG. 4 depicts the effect of mixing on IgG4 half antibody in the cell-containing (unclarified harvest) hold study. Half antibody content in percentage of total antibody molecules is shown as a function of hold time (in days) either with mixing (circles with dotted lines) or without mixing (circles with solid lines) by gentle rotation. Samples were held at 8° C. Initial cell viability for both conditions was approximately $2.5 \times 10^6$ cells/mL.

The effect of mixing the cell-containing solution on the level of IgG4 half antibody was also studied (FIG. 4). The low initial viable cell density sample (from FIG. 3, graph C) was held either in (1) static, non-mixed condition, or (2) continuously mixed using a rotator. Mixing the unclarified harvest solution was able to significantly accelerate the decrease in half antibody, achieving approximately 13% half antibody after two weeks of hold at 8° C. compared to greater than 20% half antibody without any mixing at these same time and temperature conditions (FIG. 4).

Example 6. Addition of Redox Reagents to Cell-Containing System: Evaluation of Unclarified Harvest In order to further accelerate the conversion of half antibody to full antibody, redox reagents, specifically reduced and oxidized glutathione, were directly added to a cell-containing system, unclarified harvest, followed by purification and analytical evaluation. The unclarified harvest sample was held at 8° C.

In a first experiment, the initial cell viability in the unclarified harvest sample was low at only $2.5 \times 10^6$ cells/mL. Although this low cell viability condition did not exhibit any change in half antibody in the absence of glutathione (FIG. 5, circles), the addition of glutathione, whether with 5 mM oxidized glutathione and 0.5 mM reduced glutathione (FIG. 5, squares) or with 0.5 mM oxidized glutathione and 5 mM reduced glutathione (FIG. 5, triangles), significantly decreased the half antibody and did so much more rapidly than in any of the redox reagent-free conditions studied.

As shown in FIG. 5, the lowest half antibody level achieved was for the condition with 0.5 mM reduced glutathione and 5 mM oxidized glutathione within approximately 4 days of hold in cell-containing harvest conditions at 8° C. (FIG. 5, triangles). It is possible that the low half antibody content was achieved at a time earlier than 4 days. However, the earliest time point measurement for these conditions was four days. For the condition with a higher level of reduced glutathione (ratio of 5 mM reduced glutathione to 5 mM oxidized glutathione), significantly decreased half antibody was also observed, although only after a longer incubation period of two weeks. (FIG. 5, squares).

Figure 6:
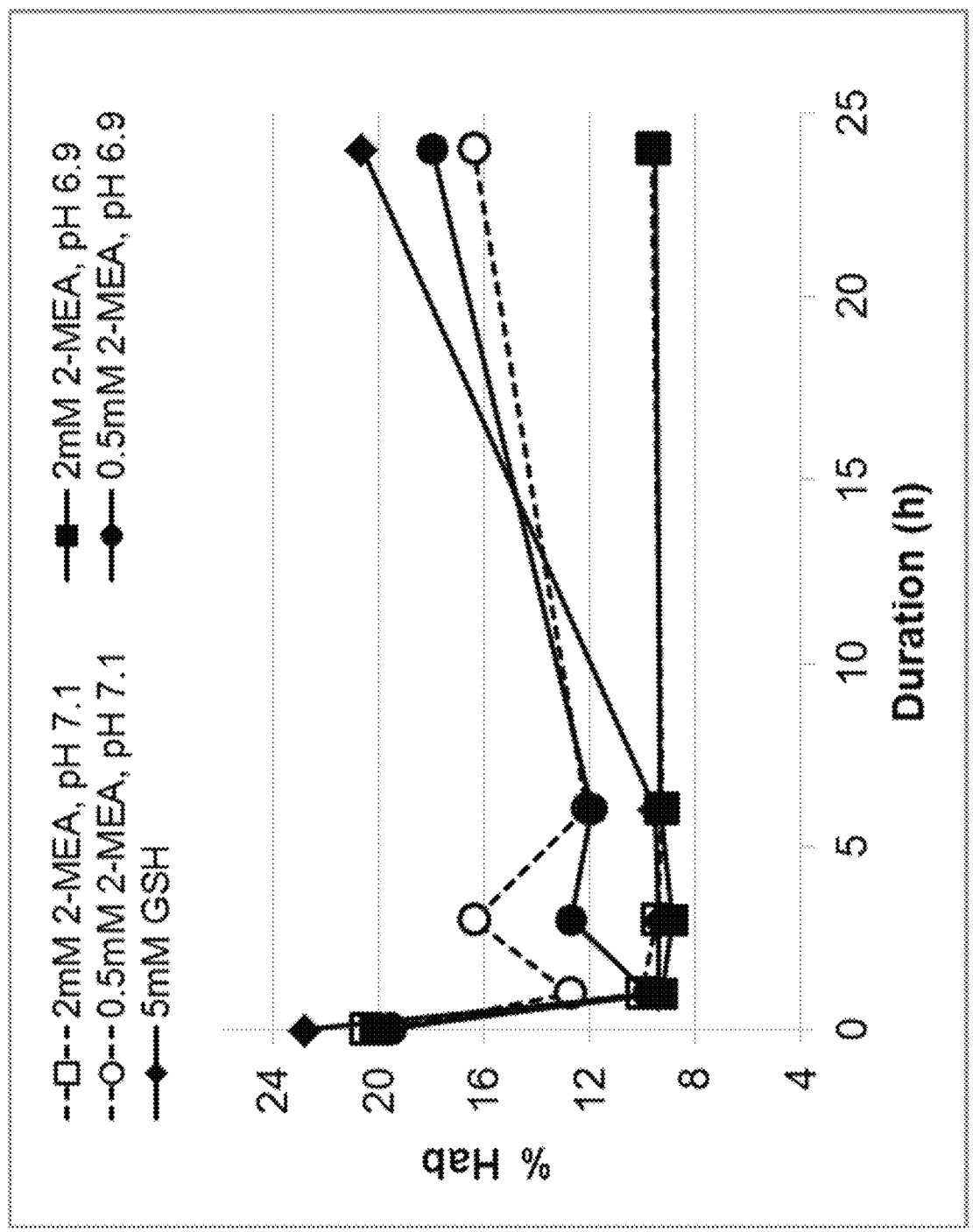
FIG. 6 depicts the effect of the addition of 0.5 mM 2-MEA, 2 mM 2-MEA, and 5 mM reduced glutathione (GSH) redox reagents to the bioreactor nearing its end of run at both high pH (7.1) and low pH (6.9) set points. Half antibody content in percentage of total antibody molecules is shown as a function of hold time (in hours) at the conditions of 2 mM 2-MEA addition at pH 7.1 (open squares) or pH 6.9 (filled squares), 0.5 mM 2-MEA addition at pH 7.1 (open circles) or pH 6.9 (filled circles), or 5 mM reduced glutathione (GSH) addition (filled diamonds). The data series for the open and closed squares nearly overlap one another.

Example 7. Addition of Redox Reagents to Cell-Containing System: During Bioreactor Operation In a second experiment, another redox reagent, 2-MEA, was evaluated by directly adding the 2-MEA into a different cell-containing system present within the bioprocess, a bioreactor. The effect of bioreactor pH on half antibody control using redox reagents was also investigated. Specifically, 0.5 mM and 2 mM 2-MEA as well as 5 mM reduced glutathione (GSH) were investigated in bioreactor cultures by adding the redox reagent together with two levels of pH (high pH: 7.1, low pH: 6.9). The results of this study are shown in FIG. 6. The pH of the culture was determined to not have an impact on the Hab conversion and Hab stability, indicating that the Hab conversion via addition of redox reagents was robust with respect to pH for the conditions tested within the bioreactor cell-containing system.

These studies of half antibody proportion within the cell-containing bioreactor indicated that 2-MEA was the most effective redox agent tested, and that a concentration of 2 mM 2-MEA was effective in controlling the proportion of Hab to within 8-10% for at least 24 hr (FIG. 6, squares and triangles) in the bioreactor. For all of the conditions tested, the proportion of Hab decreased significantly during the earliest time after the redox reagent addition, reaching below 10% for all but one of the conditions (FIG. 6). Interestingly, for all conditions except the 2 mM 2-MEA, the proportion of Hab increased over time to levels nearing the initial level of Hab. (FIG. 6). The reversion back to half antibody was the most rapid for 0.5 mM 2-MEA, indicating that the concentration of the redox reagent may be a key parameter in controlling the proportion of Hab in an antibody solution.

Figure 7:
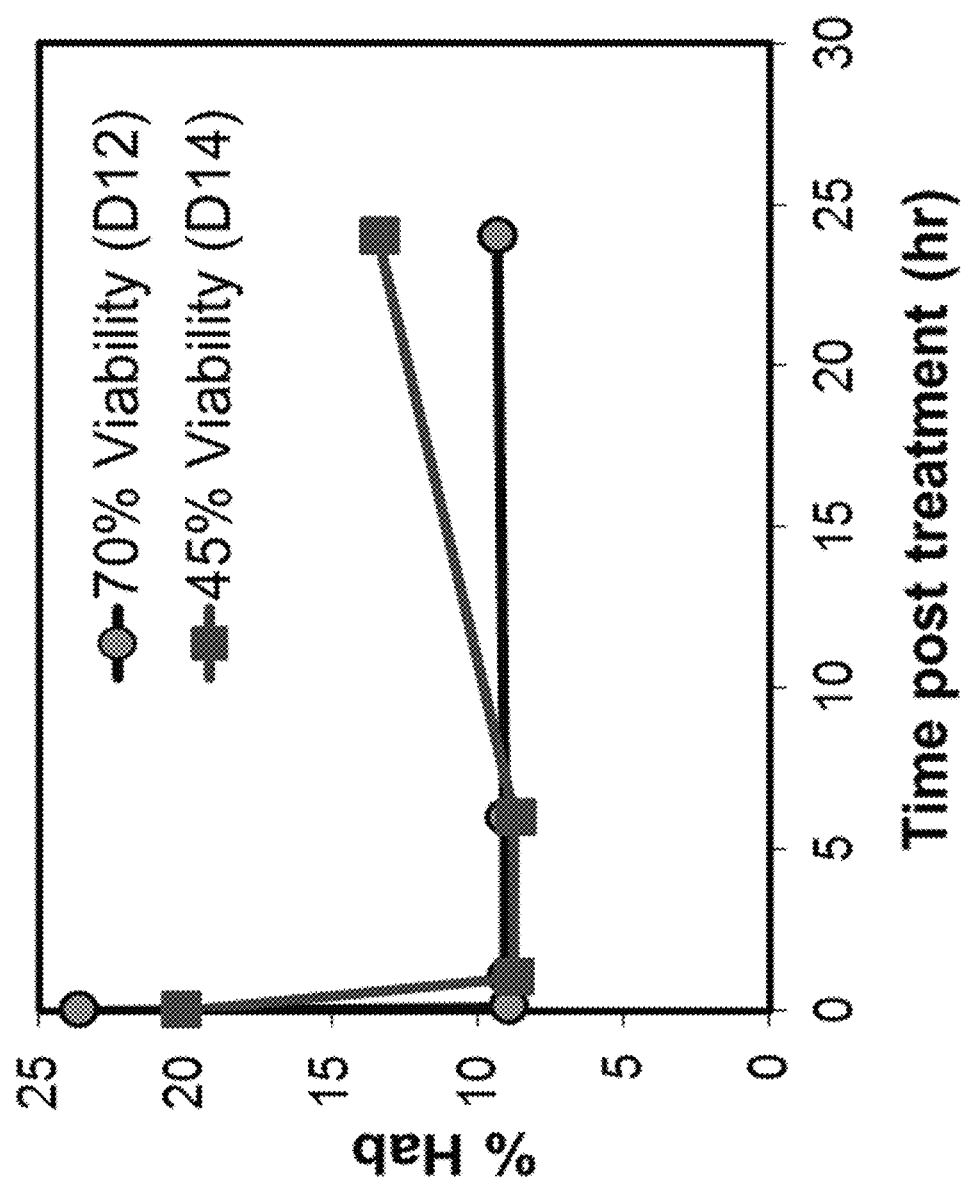
FIG. 7 depicts the effect of two different initial cell viabilities on the proportion of half antibody treated with 2-MEA. Half antibody content in percentage of total antibody molecules is shown as a function of hold time post treatment (in hours). Samples were obtained from the bioreactor, which was controlled to specified levels for various parameters. The two different initial viabilities that were studied were 70% viability at day 12 (D12) of the fed-batch culture (circles) and 45% viability at day 14 (D14) of the fed-batch culture (squares).

Additional experiments were also performed to determine the potential effect of initial cell viability within the bioreactor on the progression of Hab and the capability of 2-MEA to achieve Hab proportion control. In this study, 2 mM 2-MEA was added to two separate bioreactors nearing the end of the run of a fed-batch bioreactor campaign with a cell viability of either 70% or 45% (days 12 and 14, respectively). In both bioreactors, addition of the 2-MEA was able to decrease Hab proportion to below 10% almost immediately after addition. (FIG. 7). Consistent with observations related to cell viability described above, the Hab proportion as a function of time within the bioreactor was dependent on the initial cell viability at the time of 2-MEA addition. At a lower initial viability (45%), the Hab proportion increased from 8% to 14% after 24 hours of exposure to 2-MEA in the bioreactor (FIG. 7, squares). However, the culture with higher initial viability (70%) yielded a stable Hab profile over 24 hours of exposure to 2-MEA in the bioreactor (FIG.

7, circles). These results indicated the viable cell density of the culture in a bioreactor can impact the stability of the Hab conversion to full antibody.

Figure 8:
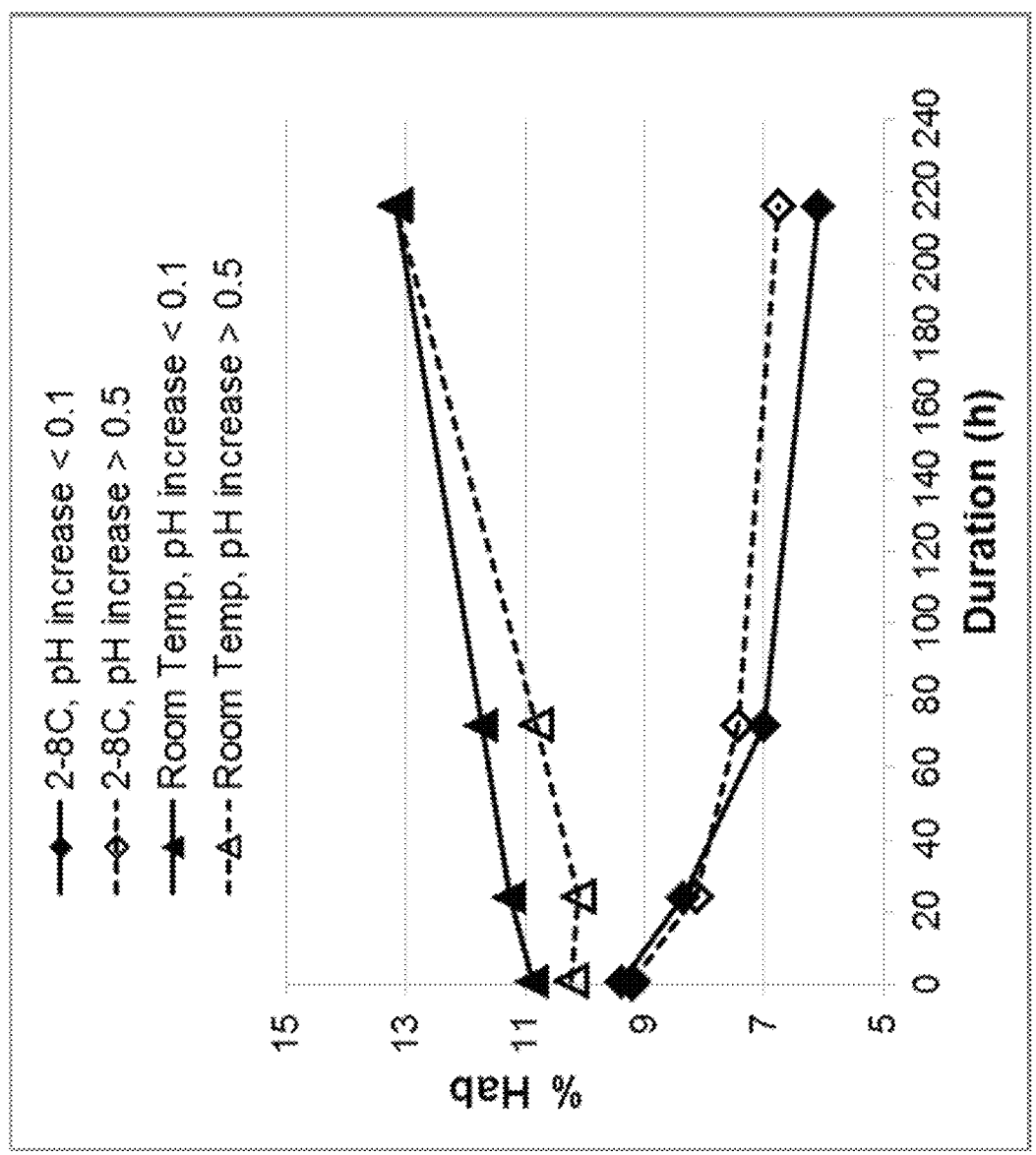
FIG. 8 depicts the effect of the temperature and pH conditions on clarified harvest obtained from a bioreactor previously treated with 2-MEA. Half antibody content in percentage of total antibody molecules is shown as a function of hold time (in hours) as a function of hold at 2-8° C. with a pH increase of less than 0.1 (filled diamonds) or a pH increase of greater than 0.5 (open diamonds), or at room temperature (21° C.) with a pH increase of less than 0.1 (filled triangles) or a pH increase of greater than 0.5 (open triangles).

Example 8. Addition of Redox Reagents to Cell-Containing System: Evaluation of Stability after Cell Removal The stability of the Hab conversion to full antibodies using redox reagents in a cell-containing system was also evaluated after removal of the cells to yield the clarified harvest for the corresponding samples by removing cells and cell debris from unclarified harvest samples. In this study, a cell-containing system (bioreactor) was treated with 2 mM 2-MEA for 24 hours. A sample of unclarified harvest was taken from the cell-containing system and was then clarified to remove the cells and cell debris, therefore yielding clarified harvest. The Hab proportion was monitored in aliquots of the clarified harvest sample held under various conditions in an incubator, including two temperatures (either 2-8° C. or 21° C./room temperature), with different magnitudes of pH increase via gas headspace manipulation. The results are shown in FIG. 8.

The results of these measurements indicate that temperature could serve as another parameter for half antibody control. For example, when the 2-MEA-treated clarified harvest was held at 2-8° C., the proportion of Hab decreased from 9-10%, measured at the start of the hold time (t=0), to 6% over the course of seven days. (FIG. 8, solid and open diamonds). Conversely, the proportion of Hab in 2-MEA-treated clarified harvest actually increased over the course of seven days when held at room temperature (21° C.) (FIG. 8, solid and open triangles).

No difference was observed between the clarified harvest samples that were stored with no headspace (FIG. 8, solid triangles/diamonds) and those that were stored with headspace. (FIG. 8, open triangles/diamonds). The results of this particular experiment indicated that pH drift did not affect Hab proportions of the 2-MEA-treated clarified harvest under the conditions studied.

These studies demonstrate that addition of redox reagents such as 2-MEA and glutathione directly to a cell-containing bioreactor near the end of the run can be used to control the proportion of half antibody present in the process. Additionally, these studies using redox reagents have evaluated the impact of selected parameters on Hab proportion control, including redox reagent identity and concentration, pH, and cell viability.

Figure 9:
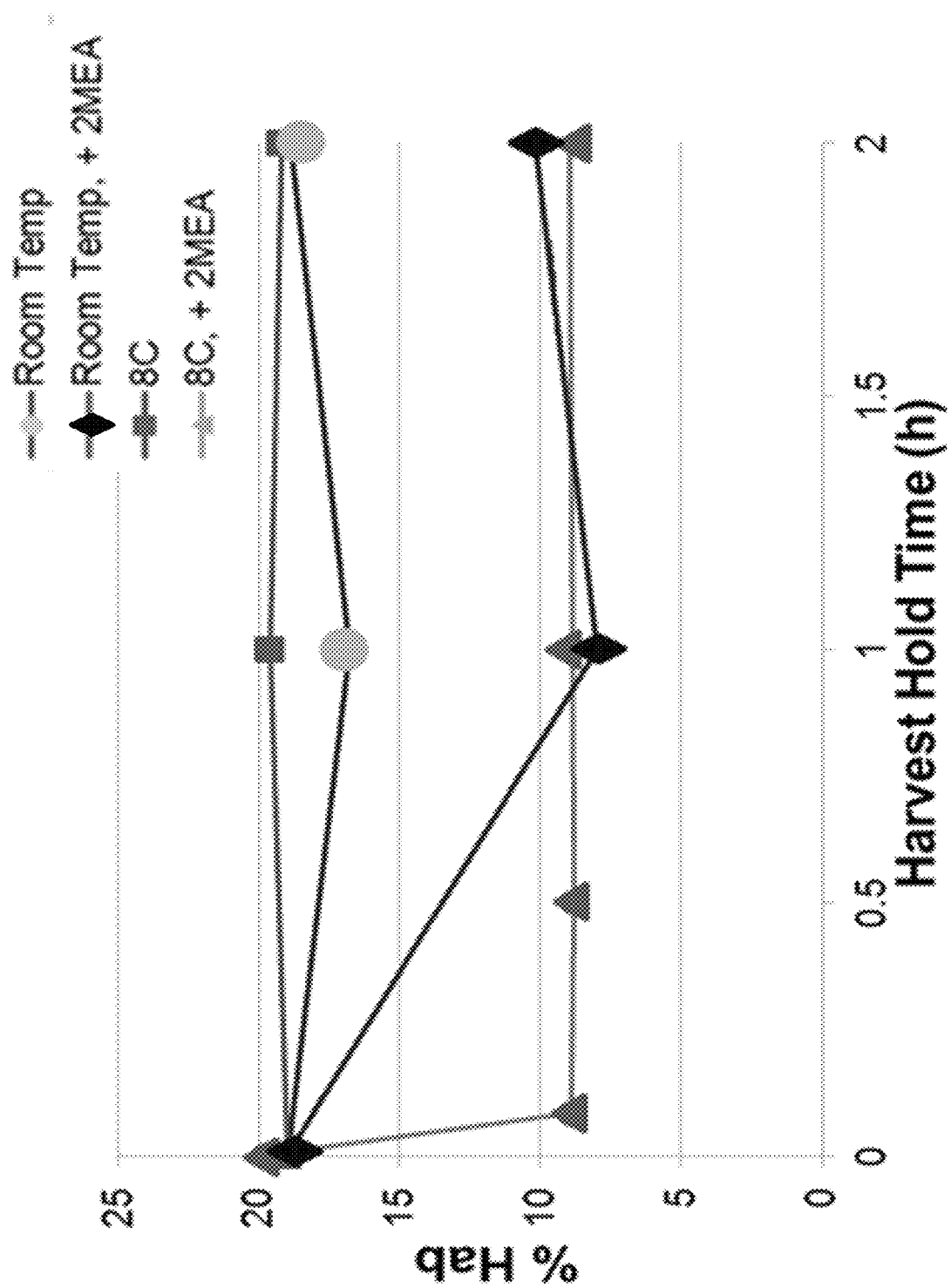
FIG. 9 depicts the effect of 2-MEA treatment on half antibody proportion in clarified harvest material after an incubation hold at room temperature (21° C.) or 8° C.
Figure 10:
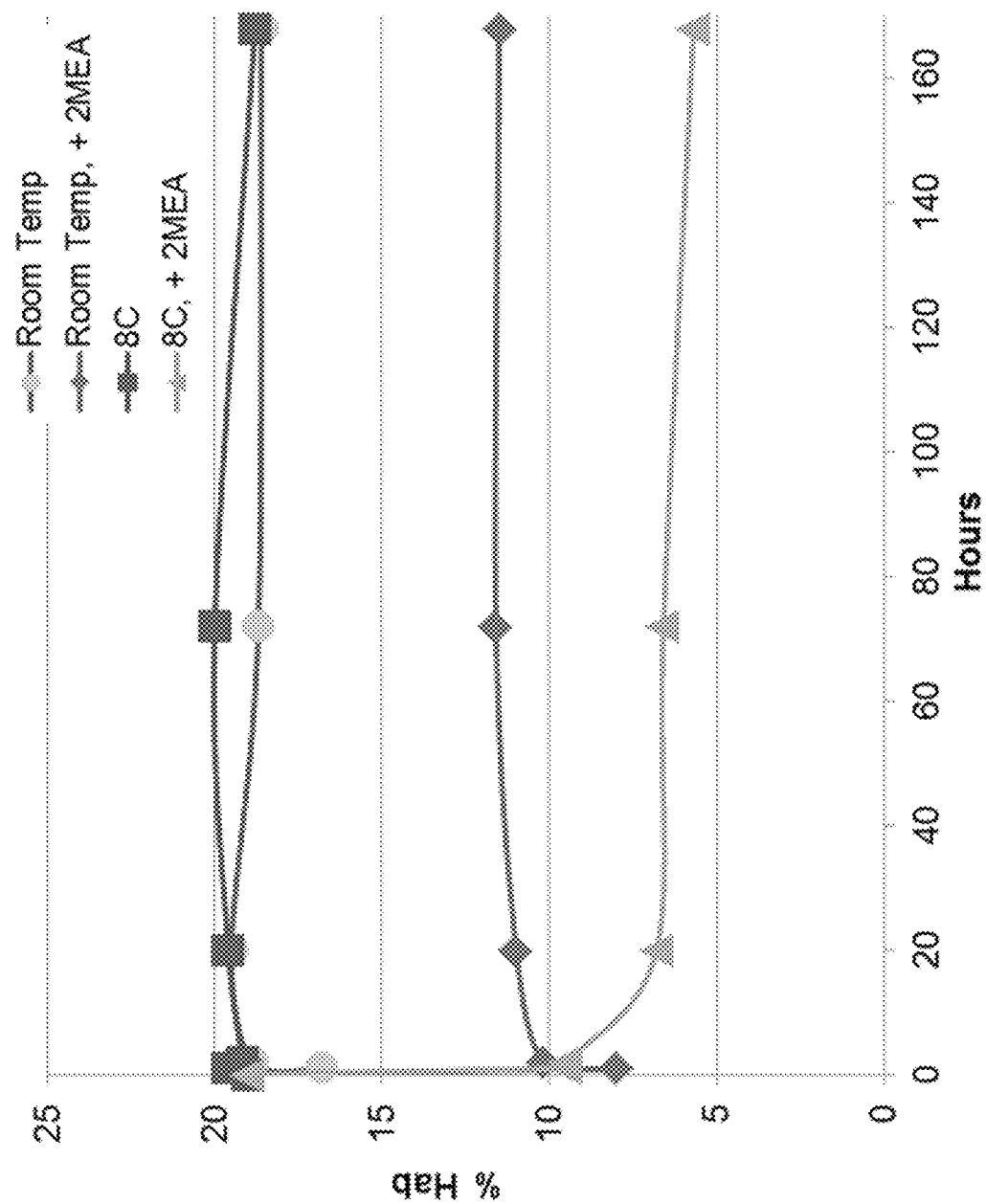
FIG. 10 depicts the effect of 2-MEA treatment on half antibody proportion in clarified harvest material after an incubation hold at room temperature (21° C.) or 8° C.

Example 9. Controlling the Proportion of IgG4 Half Antibody in a Cell-Free System: Evaluation of Addition of Redox Reagents to Clarified Harvest Studies were performed to further evaluate direct 2-MEA addition to clarified harvest material, which is a cell-free sample. In these experiments, clarified samples received either 2 mM 2-MEA or no redox reagent, followed by an incubation hold at either 2-8° C. or room temperature (21° C.). The proportion of Hab was determined over 7 days (168 hours) of incubation. The results for the first 2 hours are shown in FIG. 9, and the results out to 7 days are shown in FIG. 10. These results indicate that addition of 2-MEA followed by incubation at 8° C. can significantly decrease the Hab proportion to below 10% (FIG. 9, triangles) and that the Hab proportion remains below 10% for at least 7 days (FIG. 10, triangles). For the samples containing 2-MEA that were incubated at room temperature (21° C.), the Hab proportion also rapidly decreased almost immediately after addition of 2-MEA (FIG. 9, diamonds). However, the Hab level increased soon after the initial decline reaching a consistent level of approximately 11% Hab for incubation days 1-7 (FIG. 10, diamonds). In the control samples, material stored at either 8° C. or room temperature (21° C.) without 2-MEA did not change in Hab proportion (FIG. 9, squares; FIG. 10, circles).

This study indicates that redox reagents like 2-MEA may be added directly to cell-free systems such as clarified harvest to achieve half antibody control. Also, this option represents an additional stage within the bioprocess when Hab proportions can be controlled. The impact of temperature on clarified harvest treated with 2-MEA was also studied and found to be consistent with the results observed above for clarified harvest samples where the 2-MEA was added earlier in the process to the cell-containing system bioreactor. The ability to control Hab proportion using redox reagents like 2-MEA at multiple time points in the process provides flexibility when designing a bioprocess with sufficient control of Hab proportions.

Example 10. Confirmation of Product Quality

Several samples from clarified and unclarified harvests that had been subjected to 2-MEA treatment according to the Examples above were analyzed for a variety of product quality attributes, including glycosylation profile, charged variants, mass spectrophotometric profiles, and purity by gel electrophoresis. In all cases, no differences were observed between untreated and treated samples other than the level of half antibody present in the sample (data not shown).

Example 11. Controlling the Proportion of IgG4 Half Antibody in a Cell-Free System: Evaluation of Post-Capture Solution Overall Approach Reducing and oxidizing agents were studied in order to evaluate the ability to control the level of IgG4 half antibody in a cell-free system. In the present study, capture Protein A eluate (post-capture solution) purified from the cell culture harvest material was used to study control parameters that affect the level of half-antibody. It was hypothesized that reducing agents such as 2-mercaptoethylamine (2-MEA) could be effective in decreasing half antibody content in antibody samples. Studies to optimize the conditions to decrease half antibody were performed, evaluating incubation conditions such as pH, time, temperature, concentration of 2-MEA, and concentration of IgG4.

Materials, Methods and Analytical Techniques

Figure 11:
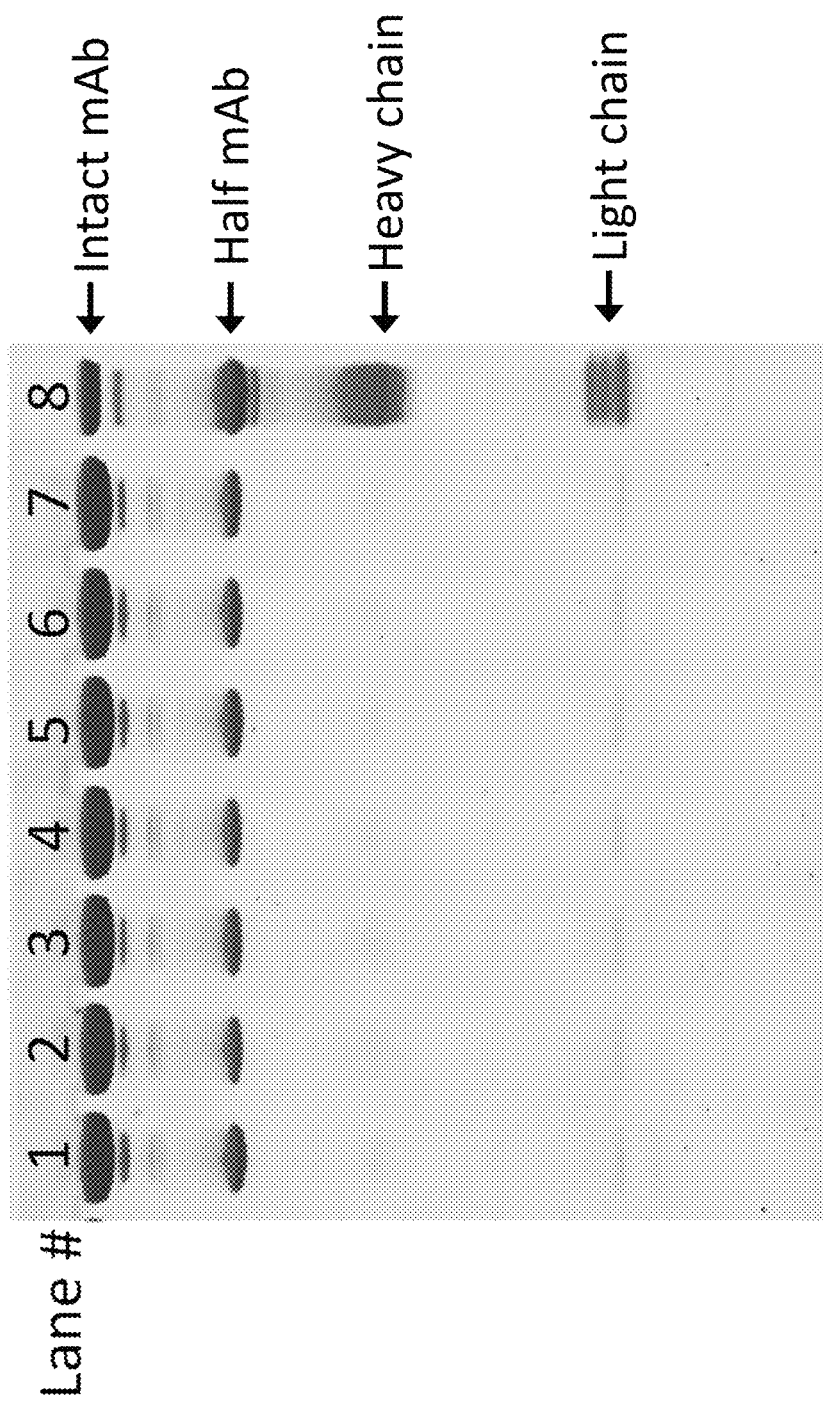
FIG. 11 depicts the results of a non-reducing sodium dodecyl sulfate polyacrylamide gel electrophoresis (SDS-PAGE) for the evaluation of various redox reagents for their ability to control the proportion of half antibody present within a bioprocess. Redox reagents were added to Protein A eluate and incubation was performed for 2 hours at room temperature at pH 4.8. All samples were re-purified on a Protein A column to remove any redox reagent present. Test conditions included no redox reagent (Lane 1), 2 mM 2-MEA (Lane 2), 3 mM 2-MEA (Lane 3), 2 mM MEA+2 mM oxidized glutathione (GSSG) (Lane 4), 2 mM reduced glutathione (GSH) (Lane 5) 2 mM GSH+2 mM GSSG (Lane 6), 2 mM mercaptoethanol (Lane 7), and 2 mM dithiothreitol (Lane 8).

Experimental procedure: Unclarified harvest material collected from fed-batch culture of an IgG4 antibody, clarified by filtration, and then purified using a column packed with MabSelect Sure Protein A resin (GE Healthcare). The Protein A eluate was adjusted to the indicated experimental conditions, incubated and then re-purified by using PreDictor RoboColumns (200 uL) packed with MabSelect SuRe Protein to remove any added reducing or oxidation reagents. Non-reduced SDS gel analysis was performed on Protein A RoboColumn re-purified eluates by using 4-20% Tris glycine gel obtained from Invitrogen. Staining of the gels was performed with Simply Blue SafeStain (Life Technologies Cat # LC6065). The level of half-antibody was measured from the scanned gel image and quantified by a densitometer. An example gel is depicted in FIG. 11.

Example 12. Addition of Redox Reagents to Cell-Free System: Evaluation of Post-Capture Solution Several reducing and oxidation reagents were tested for their ability to decrease or increase the level of half antibody present in the IgG4 population of a post-capture solution. 2-MEA was the most effective in terms of lowering the level of IgG4 half-antibody in Protein A eluate (post-capture solution) compared to the other reducing agents tested, which included 2-mercaptoethanol, and reduced glutathione (GSH). The pH was held constant at 4.8 for all redox reagent test conditions during this screening study. Redox reagent dithiothreitol (DTT) was also tested but proved unsuitable for use according to the described methods. It was observed that DTT reduced the intact IgG4 antibody to heavy and light chain fragments and also increased the levels of half antibody (FIG. 11, Lane 8). The percentage of Hab in the DTT sample could not be precisely calculated due to the presence of heavy and light chain fragments. The results are shown in Table 1 and further shown in FIG. 11.

Interestingly, addition of oxidized glutathione (GSSG) to the protein A eluate had no measurable impact on the observed half-antibody decrease in the presence of either 2-MEA or reduced glutathione (Table 1).

TABLE 1

Evaluation of various redox reagents on controlling the level of half-antibody. Lane # corresponds to the gel depicted in FIG. 11.

| Sample | Lane # | Half-antibody (%) |
|---|---|---|
| Protein A eluate | 1 | 24.5 |
| Protein A eluate + 2 mM 2-MEA | 2 | 16.2 |
| Protein A eluate + 3 mM 2-MEA | 3 | 16.9 |
| Protein A eluate + 2 mM 2-MEA + 2 mM GSSG | 4 | 16.6 |
| Protein A eluate + 2 mM GSH | 5 | 21.3 |
| Protein A eluate + 2 mM GSH + 2 mM GSSG | 6 | 20.6 |
| Protein A eluate + 2 mM 2-mercaptoethanol | 7 | 18.4 |
| PA eluate + 2 mM DTT | 8 | N/A* |

*Generated heavy and light chain fragments. Thus half antibody proportion was not quantified.

Example 13. Effect of Concentration of Redox Reagent 2-MEA on Proportion of Half Antibody 2-MEA was shown to be the most effective reducing agent tested for reducing Hab content and thus was selected for further experimentation. In order to assess 2-MEA impact on product quality, Protein A eluate (approximately 9-10 mg/ml total antibody) without and adjusted with 2-MEA (at optimum conditions) was evaluated. These experiments were designed to investigate the effect of 2-MEA concentration on the level of half-antibody in the clarified samples. The concentrations of 2-MEA tested are listed in Table 2 and ranged from 0 mM to 50 mM. In the absence of any 2-MEA (0 mM), the Hab content was observed to be 27% (Table 2). However, at concentrations of 2-MEA between 0.5 and 5 mM, the level of IgG4 half-antibody in the samples was decreased (Table 2, bold rows). Most notably, the level of half antibody decreased from 27% to 15.2% in the presence of 1 mM 2-MEA. Higher concentrations of 2-MEA (25 mM and 50 mM) resulted in increased levels of half-antibody (46 and 58%) and also generated heavy and light chain fragments (Table 2).

Interestingly, the half antibody level decreased within approx. 30 minutes in the presence of 2-MEA (1, 2 and 3 mM at pH 4.8). Similar magnitude of decrease was observed for 5, 15 and 22 hours incubation, which indicated that equilibrium conditions were achieved rapidly and that extended incubation was not beneficial (results not shown).

TABLE 2

The impact of 2-MEA concentration on the level of half antibody in Protein A Eluate.

| Concentration of 2-MEA (mM) | Half antibody (%) |
|---|---|
| 0 | 27 |
| 0.5 | 16.7 |
| 1 | 15.2 |
| 2 | 16.3 |
| 5 | 24.8 |
| 25 | 46.1 |
| 50 | N/A * |

* Generated heavy and light chain fragments. Thus half antibody proportion was not quantified.

Example 14. Effect of pH on Proportion of Half Antibody

The effect of pH of the clarified antibody sample on the half antibody level was also studied. Antibody samples containing 2-MEA concentrations of 0 mM or 2 mM were tested at pH values of 4.0, 4.8, or 7.

For the antibody samples containing 2-MEA at 2 mM, the decrease in the level of half antibody was much greater at lower pH (4.0 and 4.8) than neutral pH 7.0 (Table 3). At pH 4, the half antibody level decreased from 27.1% in the absence of 2-MEA (0 mM) to 20.8% in a solution comprising a concentration of 2 mM 2-MEA. (Table 3). At pH 4.8, the half antibody level decreased from 28.9% in the absence of 2-MEA (0 mM) to 20.4% in a solution comprising a concentration of 2 mM 2-MEA. (Table 3). However, at pH 7, the half antibody level decreased from 27.4% in the absence of 2-MEA (0 mM) to only 24.5% in a solution comprising a concentration of 2 mM 2-MEA. (Table 3).

Addition of sodium chloride to a concentration of 40 mM in the protein A eluate solution had no measurable impact on the level of half antibody decrease in the presence of 2 mM 2-MEA at pH 4.8 or neutral pH 7.0 (Table 3).

TABLE 3

Impact of pH and sodium chloride concentration on controlling the level of half antibody

| pH | 2-MEA (mM) | NaCl (mM) | Half antibody (%) |
|---|---|---|---|
| 4 | 0 | 0 | 27.1 |
|  | 2 | 0 | 20.8 |
| 4.8 | 0 | 0 | 28.9 |
|  | 2 | 0 | 20.4 |
|  | 2 | 40 | 20.4 |
| 7 | 0 | 0 | 27.4 |
|  | 2 | 0 | 24.5 |
|  | 2 | 40 | 25.8 |

The half antibody level decreased within 30 minutes in the presence of 2-MEA (1, 2 and 3 mM at pH 4.8). Similar results with extended incubation time (5, 15 and 22 hours) indicated that equilibrium conditions were achieved rapidly (data not shown).

Example 15. Critical Factor Identification

Figure 12:
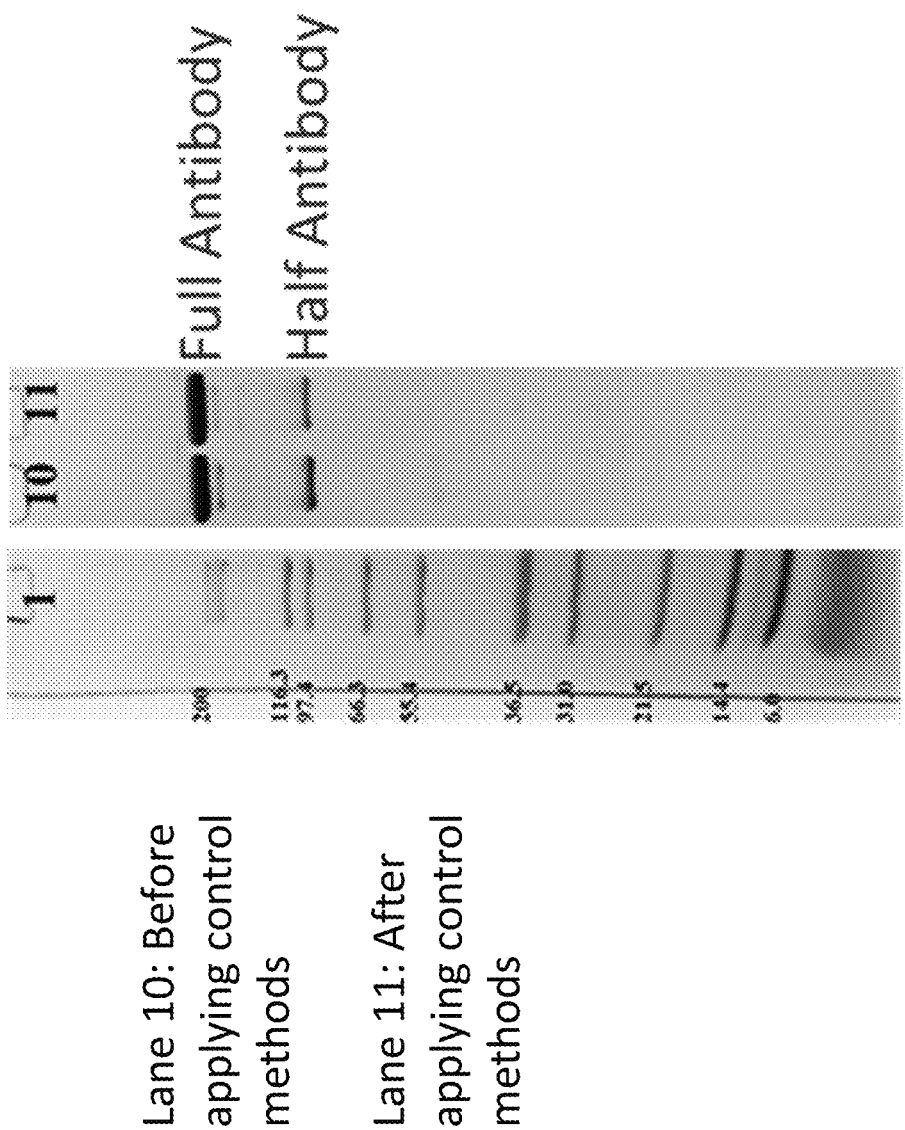
FIG. 12 depicts a non-reducing sodium dodecyl sulfate polyacrylamide gel electrophoresis (SDS-PAGE) image for analysis of an IgG4 antibody. Under denaturing conditions, such as those in SDS-PAGE, half antibodies appear as distinct bands separate from full antibodies. Lane 1: Molecular weight markers, Lane 10: IgG4 test sample before treatment with half antibody control method, Lane 11: IgG4 test samples treated with half antibody control method designed to decrease total half antibody.

In order to identify the critical factor(s) affecting half antibody levels in clarified Protein A eluate solution in the presence of 2-MEA, a full two-level factorial experiment was performed with five factors: pH, temperature, incubation time, concentration of reducing agent (2-MEA) and concentration of IgG4. Low and high values for the five factors were selected based on the experimental results disclosed in the above examples, as well as various other range-finding and optimization experiments performed previously. The values tested in these experiments are shown below in Table 4, and a representative gel is shown in FIG. 12.

TABLE 4

Low and High Set Points for 2-Level Full-Factorial Design with 5 centerpoint replicates.

| | Low | High | Centerpoint |
|---|---|---|---|
| pH (units) | 3.4 | 6 | 4.7 |
| Temp (° C.) | 8 | 22 | 15 |
| Time (h) | 0.5 | 6 | 3.25 |
| 2-MEA (mM) | 0.5 | 3 | 1.75 |
| IgG4 (mg/ml) | 4 | 20 | 12 |

Thirty-seven samples were tested. The initial level of half antibody measured in the Protein A eluate (18.5%) was decreased to 8-9% within 30 minutes at pH 3.4 in the presence of low concentrations of 2-MEA (0.5 and 3 mM). In this particular example, the additional factors studied, including temperature, time, 2-MEA concentration, and IgG4 concentration, were not shown to have a statistically significant effect on the level of half antibody over the ranges studied.

Collectively, these results indicate that the level of IgG4 half antibody could be effectively controlled by addition of the redox reagent 2-MEA to a post-capture solution such as Protein A eluate.

What is claimed is:

1. A method of controlling the number of disulfide bonds between polypeptides of a multimeric protein produced by a bioprocess, the method comprising:
   (a) contacting the polypeptides with a conditioned solution at a specific time point during the bioprocess, wherein the conditioned solution comprises a redox reagent, and
   (b) incubating the conditioned solution comprising the polypeptides for a predetermined time at a predetermined temperature;
   wherein the incubation of the polypeptides with the conditioned solution controls the formation of disulfide bonds between the polypeptides of the protein;
   wherein the number of disulfide bonds between the polypeptides of the protein is increased;
   wherein the redox reagent is 2-mercaptoethylamine (2-MEA);
   wherein the conditioned solution has a pH between 3.4 to 6; and
   wherein the predetermined temperature of the incubation is between 2° C. and 8° C.

2. The method of claim 1, wherein the number of disulfide bonds between the polypeptides of the protein is decreased.

3. The method of claim 1, wherein the number of disulfide bonds between the polypeptides of the protein is maintained.

4. The method of claim 1, wherein the ratio of redox reagent molarity to protein molarity is at least about 4:1, 8:1, 16:1, or 32:1.

5. The method of claim 1, wherein the conditioned solution comprising the polypeptides is mixed during incubation.

6. The method of claim 1, further comprising:
   removing the polypeptides from the bioprocess at the specific time point during the bioprocess.

7. The method of claim 6, further comprising:
   returning the polypeptides to the bioprocess after incubation.

8. The method of claim 1, wherein the bioprocess comprises a batch, semi-continuous, or continuous bioprocess.

9. The method of claim 1, wherein the specific time point during the bioprocess comprises a time point after a bioreactor operation or fed batch cell culture operation in the bioprocess.

10. The method of claim 1, wherein the specific time point during the bioprocess comprises a time point wherein the polypeptides are in a solution comprising a plurality of cells.

11. The method of claim 10, wherein the specific time point during the bioprocess comprises a time point wherein the polypeptides are located in a bioreactor, holding tank, or a non-bioreactor unit operation vessel comprising a plurality of cells.

12. The method of claim 1, wherein the specific time point during the bioprocess comprises a time point wherein the polypeptides are in a cell-free solution.

13. The method of claim 12, wherein the specific time point during the bioprocess comprises a time point wherein the polypeptides are located in a holding tank.

14. The method of claim 12, wherein the specific time point during the bioprocess comprises a time point during the step of viral inactivation, adjustment, chromatography, filtration, dilution, concentration, or any bioprocess step that is cell-free.

15. The method of claim 12, wherein the specific time point during the bioprocess comprises a time point during the clarification stage, clarified harvest stage, capture stage, intermediate chromatography stage, or polishing chromatography stage of the bioprocess.

16. The method of claim 12, wherein the cell-free solution comprises clarified harvest.

17. The method of claim 12, wherein the cell-free solution comprises Protein A eluate.

18. The method of claim 1, wherein the multimeric protein is a non-antibody protein.

19. The method of claim 1, wherein the multimeric protein is an antibody.

20. The method of claim 1, wherein the multimeric protein is an antibody fragment.

21. The method of claim 19 or 20, wherein the polypeptides of the multimeric protein comprise heavy chain polypeptides.

22. The method of claim 19 or 20, wherein the polypeptides of the multimeric protein comprise light chain polypeptides.

23. The method of claim 19 or 20, wherein the polypeptides of the multimeric protein comprise heavy chain polypeptides and light chain polypeptides.

24. The method of claim 1, wherein the polypeptides are monomers or multimers of the protein.

25. A method of controlling the proportion of half antibody molecules in a solution comprising a population of antibody molecules, the method comprising:
   (a) contacting the solution comprising the population of antibody molecules with a conditioned solution, wherein the conditioned solution comprises a redox reagent; and (b) incubating the conditioned solution comprising the antibody molecules for a predetermined time at a predetermined temperature;

wherein the incubation of the antibody molecules with the conditioned solution regulates the proportion of half antibody molecules in the conditioned antibody solution;

wherein the regulation of the proportion of half antibody molecules consists of decreasing the proportion of half antibody molecules;

wherein the redox reagent is 2-mercaptoethylamine (2-MEA);

wherein the conditioned solution has a pH between 3.4 to 6; and wherein the predetermined temperature of the incubation is between 2° C. and 8° C.

26. The method of claim 19 or 25, wherein the antibody is an IgG4 antibody.

27. The method of claim 25, wherein the antibody is an antibody fragment.

28. The method of claim 20 or 27, wherein the antibody fragment is an IgG4 antibody fragment.

29. The method of claim 25, wherein the proportion of half antibody molecules in the conditioned antibody solution is less than 30 percent.

30. The method of claim 25, wherein the proportion of half antibody molecules in the conditioned antibody solution is less than 15 percent.

31. The method of claim 26, wherein the antibody solution comprises natalizumab, gemtuzumab, or fresolimumab.

* * * * *